US010695137B2

(12) United States Patent
Farritor et al.

(10) Patent No.: US 10,695,137 B2
(45) Date of Patent: *Jun. 30, 2020

(54) METHODS, SYSTEMS, AND DEVICES FOR SURGICAL ACCESS AND PROCEDURES

(71) Applicant: Board of Regents of the University of Nebraska, Lincoln, NE (US)

(72) Inventors: Shane Farritor, Lincoln, NE (US); Mark Rentschler, Boulder, CO (US); Amy Lehman, York, NE (US); Stephen Platt, Urbana, IL (US); Jeff Hawks, Beatrice, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 141 days.

This patent is subject to a terminal disclaimer.

(21) Appl. No.: 15/966,606

(22) Filed: Apr. 30, 2018

(65) Prior Publication Data
US 2018/0250082 A1 Sep. 6, 2018

Related U.S. Application Data

(63) Continuation of application No. 14/454,035, filed on Aug. 7, 2014, now Pat. No. 9,956,043, which is a
(Continued)

(51) Int. Cl.
*A61B 34/30* (2016.01)
*A61B 34/00* (2016.01)
*A61B 17/00* (2006.01)

(52) U.S. Cl.
CPC ........ *A61B 34/30* (2016.02); *A61B 17/00234* (2013.01); *A61B 34/70* (2016.02);
(Continued)

(58) Field of Classification Search
CPC ......... A61B 34/30; A61B 34/72; A61B 34/71; A61B 34/70; A61B 34/73;
(Continued)

(56) References Cited

U.S. PATENT DOCUMENTS 3,870,264 A 3/1975 Robinson
3,989,952 A 11/1976 Timberlake et al.
(Continued)

FOREIGN PATENT DOCUMENTS

CN 102821918 12/2012
DE 102010040405 3/2012
(Continued)

OTHER PUBLICATIONS

Franzino, "The Laprotek Surgical System and the Next Generation of Robotics," Surg Clin North Am, 2003 83(6): 1317-1320.
(Continued)

*Primary Examiner* — Mark Bockelman
(74) *Attorney, Agent, or Firm* — Davis, Brown, Koehn, Shors & Roberts, P.C.; Sean D. Solberg

(57) ABSTRACT

The embodiments disclosed herein relate to various medical device components, including components that can be incorporated into robotic and/or in vivo medical devices. Certain embodiments include various actuation system embodiments, including fluid actuation systems, drive train actuation systems, and motorless actuation systems. Additional embodiments include a reversibly lockable tube that can provide access for a medical device to a patient's cavity and further provides a reversible rigidity or stability during operation of the device. Further embodiments include various operational components for medical devices, including medical device arm mechanisms that have both axial and rotational movement while maintaining a relatively compact structure. medical device winch components, medical
(Continued)

device biopsy/stapler/clamp mechanisms, and medical device adjustable focus mechanisms.

20 Claims, 21 Drawing Sheets

Related U.S. Application Data continuation of application No. 13/329,705, filed on Dec. 19, 2011, now Pat. No. 8,828,024, which is a continuation of application No. 12/171,413, filed on Jul. 11, 2008, now Pat. No. 8,343,171.

(60) Provisional application No. 60/949,390, filed on Jul. 12, 2007, provisional application No. 60/949,391, filed on Jul. 12, 2007, provisional application No. 60/990,076, filed on Nov. 26, 2007, provisional application No. 61/025,346, filed on Feb. 1, 2008.

(52) U.S. Cl.
CPC ............. *A61B 34/71* (2016.02); *A61B 34/72* (2016.02); *A61B 34/73* (2016.02); *A61B 2017/00278* (2013.01); *A61B 2017/00539* (2013.01); *A61B 2017/00544* (2013.01); *A61B 2034/302* (2016.02); *A61B 2034/306* (2016.02)

(58) Field of Classification Search
CPC ........ A61B 17/00234; A61B 2034/306; A61B 2034/302; A61B 2017/00544; A61B 2017/00539; A61B 2017/00278
See application file for complete search history.

(56) References Cited

U.S. PATENT DOCUMENTS

| | | |
|---|---|---|
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,172,639 A | 12/1992 | Wiesman et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Ortiz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tiemey et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |

(56) References Cited

U.S. PATENT DOCUMENTS

| | | |
|---|---|---|
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B1 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |

(56) References Cited

U.S. PATENT DOCUMENTS

| | | |
|---|---|---|
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,353,897 B2 | 1/2013 | Doyle et al. |
| 9,089,353 B2 | 7/2015 | Farritor et al. |
| 2001/0018591 A1 | 8/2001 | Brook et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zadno-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |

(56) References Cited

U.S. PATENT DOCUMENTS

| | | |
|---|---|---|
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0098529 A1 | 4/2011 | Ostrovsky et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0253515 A1 | 10/2012 | Coste-Maniere et al. |
| 2013/0131695 A1 | 5/2013 | Scarfogliero et al. |
| 2013/0345717 A1 | 12/2013 | Markvicka et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| JP | 05-115425 | 5/1993 |
| JP | 2006508049 | 9/1994 |
| JP | 07-016235 | 1/1995 |
| JP | 07-136173 | 5/1995 |
| JP | 7306155 | 11/1995 |
| JP | 08-2242248 | 9/1996 |
| JP | 2001500510 | 1/2001 |
| JP | 2001505810 | 5/2001 |
| JP | 2003220065 | 8/2003 |
| JP | 2004144533 | 5/2004 |
| JP | 2004-180781 | 7/2004 |
| JP | 2004322310 | 11/2004 |
| JP | 2004329292 | 11/2004 |
| JP | 2006507809 | 3/2006 |
| JP | 2009106606 | 5/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009023851 | 2/2009 |
| WO | 2009144729 | 12/2009 |
| WO | 2010050771 | 5/2010 |
| WO | 2011075693 | 6/2011 |
| WO | 2011118646 | 9/2011 |
| WO | 2011135503 | 11/2011 |
| WO | 2013009887 | 1/2013 |
| WO | 2014011238 | 1/2014 |

OTHER PUBLICATIONS

Franklin et al., "Prospective Comparison of Open vs. Laparoscopic Colon Surgery for Carcinoma: Five-Year Results," Dis Colon Rectum, 1996; 39: S35-S46.

Flynn et al, "Tomorrow's surgery: micromotors and microrobots for minimally invasive procedures," Minimally Invasive Surgery & Allied Technologies, 1998; 7(4): 343-352.

Fireman et al., "Diagnosing small bowel Crohn's desease with wireless capsule endoscopy," Gut 2003; 52: 390-392.

Fearing et al., "Wing Transmission for a Micromechanical Flying Insect," Proceedings of the 2000 IEEE International Conference to Robotics & Automation, Apr. 2000; 1509-1516.

Faraz et al., "Engineering Approaches to Mechanical and Robotic Design for Minimaly Invasive Surgery (MIS)," Kluwer Academic Publishers (Boston), 2000, 13pp.

Falcone et al., "Robotic Surgery," Clin. Obstet. Gynecol. 2003, 46(1): 37-43.

Fraulob et al., "Miniature assistance module for robot-assisted heart surgery," Biomed. Tech. 2002, 47 Suppl. 1, Pt. 1: 12-15.

Fukuda et al., "Mechanism and Swimming Experiment of Micro Mobile Robot in Water," Proceedings of the 1994 IEEE International Conference on Robotics and Automation, 1994: 814-819.

Fukuda et al., "Micro Active Catheter System with Multi Degrees of Freedom," Proceedings of the IEEE International Conference on Robotics and Automation, May, 1994, pp. 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.

Dumpert et al., "Improving in Vivo Robot Visioin Quality," from the Proceedings of Medicine Meets Virtual Realtiy, Long Beach, CA, Jan. 26-29, 2005. 1 pg.

Dakin et al., "Comparison of laparoscopic skills pertormance between standard instruments and two surgical robotic systems," Surg Endosc., 2003; 17: 574-579.

Cuschieri, "Technology for Minimal Access Surgery," BMJ, 1999, 319: 1-6.

Grady, "Doctors Try New Surgery for Gallbladder Removal," The New York Times, Apr. 20, 2007, 3 pp.

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.

Chanthasopeephan et al., (2003), "Measuring Forces in Liver Cutting: New Equipment and Experimenal Results," Annals of Biomedical Engineering 31: 1372-1382.

Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.

(56) References Cited

OTHER PUBLICATIONS

Guber et al., "Miniaturized Instrument Systems for Minimally Invasive Diagnosis and Therapy," Biomedizinische Technic. 2002, Band 47, Erganmngsband 1: 198-201.

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

Allendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Atmel 80C5X2 Core, http://www.atmel.com, 2006, 186pp.

Bailey et al., "Complications of Laparoscopic Surgery," Quality Medical Publishers, Inc., 1995, 25pp.

Ballantyne, "Robotic Surgery, Telerobotic Surgery, Telepresence, and Telementoring," Surgical Endoscopy, 2002; 16: 1389-1402.

Bauer et al, "Case Report: Remote Percutaneous Renal Percutaneous Renal Access Using a New Automated Telesurgical Robotic System," Telemedicine Journal and e-Health 2001; (4): 341-347.

Begos et al., "Laparoscopic Cholecystectomy: From Gimmick to Gold Standard," J Clin Gastroenterol, 1994; 19(4): 325-330.

Berg et al., "Surgery with Cooperative Robots," Medicine Meets Virtual Reality, Feb. 2007, 1 pg.

Breda et al., "Future developments and perspectives in laparoscopy," Eur. Urology 2001; 40(1): 84-91.

Breedveld et al., "Design of Steerable Endoscopes to Improve the Visual Perception of Depth During Laparoscopic Surgery," ASME, Jan. 2004; vol. 126, pp. 1-5.

Breedveld et al., "Locomotion through the Intestine by means of Rolling Stents," Proceedings of the ASME Design Engineering Technical Conferences, 2004, pp. 1-7.

Calafiore et al., Multiple Arterial Conduits Without Cardiopulmonary Bypass: Early Angiographic Results,: Ann Thorac Surg, 1999; 67: 450-456.

Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," in McLaughliin, M.L, Hespanha, J.P., and Sukhatme, G., editors. Touch in virtual environments, IMSC Series in Multimedia 2001, 28pp.

Dumpert et al., "Stereoscopic In Vivo Surgical Robots," IEEE Sensors Special Issue on In Vivo Sensors for Medicine, Jan. 2007, 10 pp.

Green, "Telepresence Surgery", Jan. 1, 1995, Publisher: IEEE Engineering in Medicine and Biology.

Cleary et al., "State of the Art in Surgical Rootics: Clinical Applications and Technology Challenges", "Computer Aided Surgery", Jan. 1, 2002, pp. 312-328, vol. 6.

Stoianovici et al., "Robotic Tools for Minimally Invasive Urologic Surgery", Jan. 1, 2002, pp. 1-17.

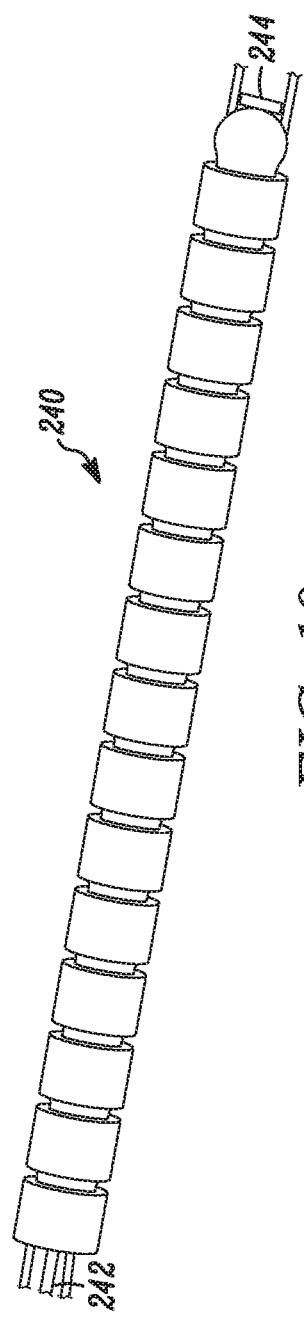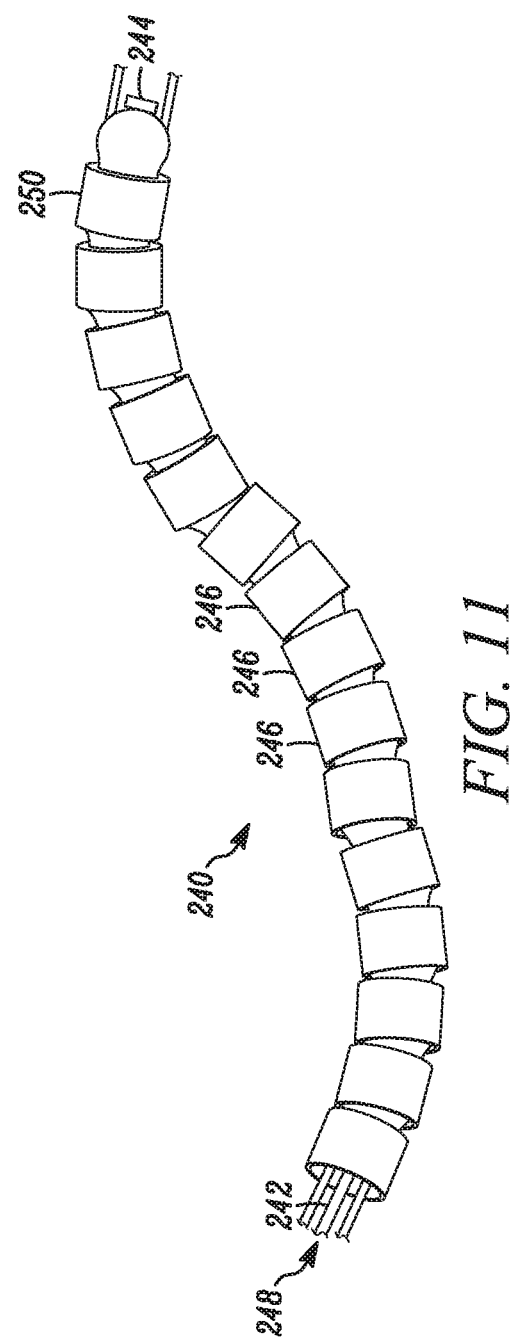

METHODS, SYSTEMS, AND DEVICES FOR SURGICAL ACCESS AND PROCEDURES

CROSS-REFERENCE TO RELATED APPLICATIONS

This application claims priority as a continuation of U.S. application Ser. No. 14/454,035, filed on Aug. 7, 2014 and entitled "Methods, Systems, and Devices for Surgical Access and Procedures," which is a continuation of U.S. Pat. No. 8,828,024, filed on Dec. 19, 2011, issued on Sep. 9, 2014, and entitled "Methods, Systems, and Devices for Surgical Access and Procedures," which is a continuation of U.S. Pat. No. 8,343,171, filed on Jul. 11, 2008, issued on Jan. 1, 2013, and entitled "Methods and Systems of Actuation in Robotic Devices," all of which are hereby incorporated by reference in their entireties. Further, U.S. Pat. No. 8,343,171 claims priority to Provisional Application No. 60/949,390, filed Jul. 12, 2007; Provisional Application No. 60/949,391, filed Jul. 12, 2007; Provisional Application No. 60/990,076, filed Nov. 26, 2007; and Provisional Application No. 61/025,346, filed Feb. 1, 2008, all of which are hereby incorporated herein by reference in their entireties.

GOVERNMENT SUPPORT

This invention was made with government support under Grant Number R21 EB056632, awarded by the National Institutes of Health. The government has certain rights in the invention.

TECHNICAL FIELD

The embodiments disclosed herein relate to various medical device components, including components that can be incorporated into robotic and/or in vivo medical devices. Certain embodiments include various actuation system embodiments, including fluid actuation systems, drive train actuation systems, and motorless actuation systems. Further embodiments include various operational components for medical devices, including medical device arm mechanisms, medical device winch mechanisms, medical device biopsy/stapler/clamp mechanisms, and medical device adjustable focus mechanisms. Other embodiments relate to reversibly lockable tube mechanisms.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

SUMMARY

One embodiment disclosed herein relates to a biopsy component having a substantially fixed jaw component, a mobile jaw component adjacent to the substantially fixed jaw component, and a sliding component configured to move between a first position and a second position. The mobile jaw component is predisposed to a position in which a distal end of the component is not in contact with the substantially fixed jaw component. Further, the sliding component in the second position is in contact with the mobile jaw component such that the sliding component urges the distal end of the mobile jaw component toward the substantially fixed jaw component.

Another embodiment disclosed herein relates to an arm device having an extendable rotational arm, a first drive component, a second drive component, a first driven component, a second driven component, and a pin. The extendable rotational arm has an exterior portion having a first coupling component and further has a first aperture defined within the arm. The first drive component is coupled with the first driven component, and the first driven component has an inner surface having a second coupling component that is configured to be coupled with the first coupling component. The second drive component is coupled with the second driven component, and the second driven component has a second aperture defined within it. The pin is disposed within the first and second apertures. According to one embodiment, the first and second coupling components are threads. In a further embodiment, the first and second drive components and first and second driven components are gears. Alternatively, the first and second drive components and the first and second driven components are a pulley system or a friction drive system.

Yet another embodiment disclosed herein relates to a medical device having a body, a first winch component and an actuation component. The first winch component has a first drum and a first tether operably coupled to the first drum. In one embodiment, the actuation component is operably coupled to the first drum. In an additional embodiment, the device further has an end effector operably coupled to the distal end of the tether. In yet another implementation, the device also has a second winch component having a second drum and a second tether operably coupled to the second drum. According to a further embodiment, the device also has a third winch component having a third drum and third tether operably coupled to the third drum.

BRIEF DESCRIPTION OF THE DRAWINGS

FIG. 10 is a front view of a reversibly lockable tube, according to one embodiment.

FIG. 11 depicts a perspective view of the reversibly lockable tube of FIG. 10.

DETAILED DESCRIPTION

Figure 1A:
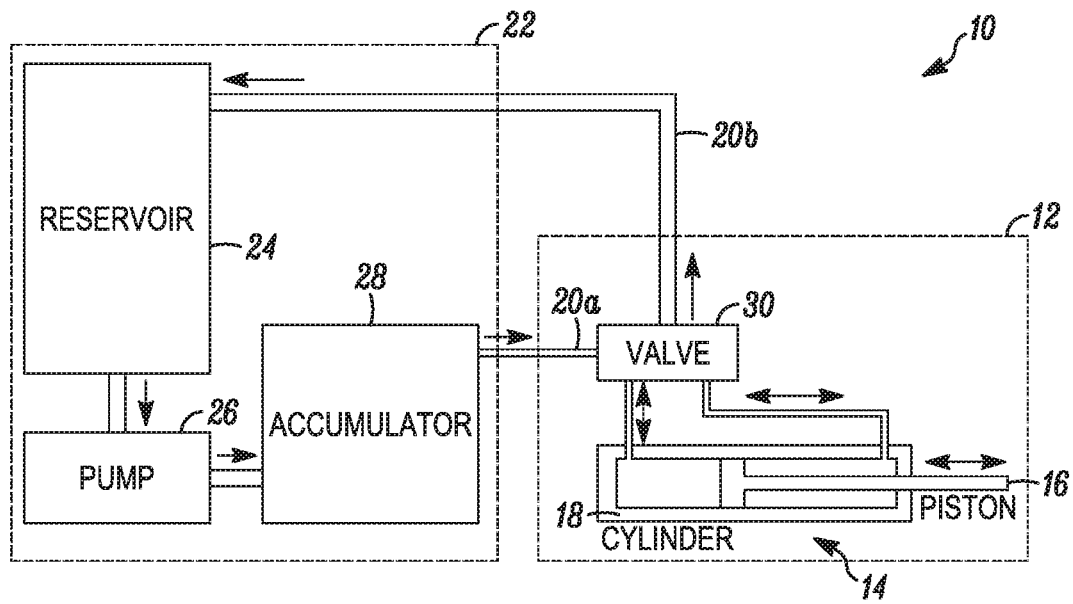
FIG. 1A is a schematic depicting a fluid actuation system, according to one embodiment.

The various systems and devices disclosed herein relate to devices for use in medical procedures and systems. More specifically, the various embodiments relate to various actuation or end effector components or systems that can be used in various procedural devices and systems.

It is understood that the various embodiments of actuation, end effector, and other types of device components disclosed herein can be incorporated into or used with any known medical devices, including, but not limited to, robotic or in vivo devices as defined herein.

For example, the various embodiments disclosed herein can be incorporated into or used with any of the medical devices disclosed in copending U.S. application Ser. Nos. 11/932,441 (filed on Oct. 31, 2007 and entitled "Robot for Surgical Applications"), 11/695,944 (filed on Apr. 3, 2007 and entitled "Robot for Surgical Applications"), 11/947,097 (filed on Nov. 27, 2007 and entitled "Robotic Devices with Agent Delivery Components and Related Methods), 11/932,516 (filed on Oct. 31, 2007 and entitled "Robot for Surgical Applications"), 11/766,683 (filed on Jun. 21, 2007 and entitled "Magnetically Coupleable Robotic Devices and Related Methods"), 11/766,720 (filed on Jun. 21, 2007 and entitled "Magnetically Coupleable Surgical Robotic Devices and Related Methods"), 11/966,741 (filed on Dec. 28, 2007 and entitled "Methods, Systems, and Devices for Surgical Visualization and Device Manipulation"), 60/949,391 (filed on Jul. 12, 2007), 60/949,390 (filed on Jul. 12, 2007), 60/990,062 (filed on Nov. 26, 2007), 60/990,076 (filed on Nov. 26, 2007), 60/990,086 (filed on Nov. 26, 2007), 60/990,106 (filed on Nov. 26, 2007), 60/990,470 (filed on Nov. 27, 2007), 61/025,346 (filed on Feb. 1, 2008), 61/030,588 (filed on Feb. 22, 2008), and 61/030,617 (filed on Feb. 22, 2008), all of which are hereby incorporated herein by reference in their entireties.

In an exemplary embodiment, any of the various embodiments disclosed herein can be incorporated into or used with a natural orifice translumenal endoscopic surgical device, such as a NOTES device. Those skilled in the art will appreciate and understand that various combinations of features are available including the features disclosed herein together with features known in the art.

Certain device implementations disclosed in the applications listed above can be positioned within a body cavity of a patient, including certain devices that can be positioned against or substantially adjacent to an interior cavity wall, and related systems. An "in vivo device" as used herein means any device that can be positioned, operated, or controlled at least in part by a user while being positioned within a body cavity of a patient, including any device that is positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments disclosed herein relate to actuation components or systems that are configured to provide motive force to any of the various procedural device embodiments described above. One such embodiment is a fluid actuation system. FIG. 1A schematically depicts one embodiment of a fluid actuation system 10 for a procedural device. According to one implementation, the fluid actuation system 10 is a hydraulic system. Alternatively, the fluid actuation system 10 is a pneumatic system. In a further alternative, the fluid actuation system can be any known such system. Hydraulic systems are generally preferred for higher power transmission, while pneumatic systems can be a good actuation system for binary actuation, such as actuation required for a grasper. In the hydraulic embodiment depicted in FIG. 1A, the system 10 includes a medical device 12 that is connected via a hydraulic connection line 20 to external hydraulic components 22. The device 12 as shown has a hydraulic piston assembly 14 having a piston 16 positioned within a cylinder 18. The piston assembly 14 can be used for any actuation associated with the device 12, such as powering movement of the device 12 in relation to the patient's body, actuating a component of the device to perform an action, or any other desired actuation.

As further shown in FIG. 1A, the piston assembly 14 is connected via a hydraulic connection line 20 to the external hydraulic components 22, which include a reservoir 24, a pump 26, and an accumulator 28. The external hydraulic components 22 are positioned at a location external to the patient's body. Thus, the hydraulic connection line 20 is connected to the piston assembly 14 in the device 12 through the valve component 30 and to the external hydraulic components 22 such that the line 20 extends from the interior of the patient's body to the exterior when the device 12 is positioned in the patient's body. According to one embodiment, the line 20a that couples the accumulator 28 to the valve component 30 is a high pressure supply line 20a that provides fluid to the valve component 30 under high pressure. In accordance with a further implementation, the line 20b that couples the valve component 30 to the reservoir 24 is a low pressure supply line 20b that allows fluid to move from the valve component 30 to the reservoir 24 under low pressure.

In one embodiment, the hydraulic fluid used in the hydraulic system 10 is saline solution. Alternatively, the fluid is water-based. In a further alternative, the hydraulic fluid can be any fluid that is non-toxic, biocompatible, and less compressible as required to provide sufficient precise control.

In one implementation, the external hydraulic components 22 are the reservoir 24, pump 26, and accumulator 28 as discussed above, which operate in known fashion to hydraulically power the piston assembly 14. In one example, the pump 26 used in this system is a commercially-available surgical irrigation pump, while the accumulator 28 and reservoir 24 are commercially available from Parker Hannifin, which is located in Cleveland, Ohio. Alternatively, the external hydraulic components 22 can be any known configuration of any hydraulic components capable of hydraulically powering the piston 16.

According to one implementation of a fluid actuation system, the piston 16 is a standard syringe handle and the cylinder 18 is the syringe body. Alternatively, the piston assembly 14 can be a small commercially available system used for model airplane landing gear. In a further embodiment, the piston 16 is custom machined with an o-ring around the piston head, while the cylinder 18 is a machined or molded cavity within the robot's base or arms.

The valve component 30 has a valve for each piston assembly 14. Thus, the valve component 30 may have anywhere from one valve to any number equal to the maximum number of valves provided in the system.

Figure 1B:
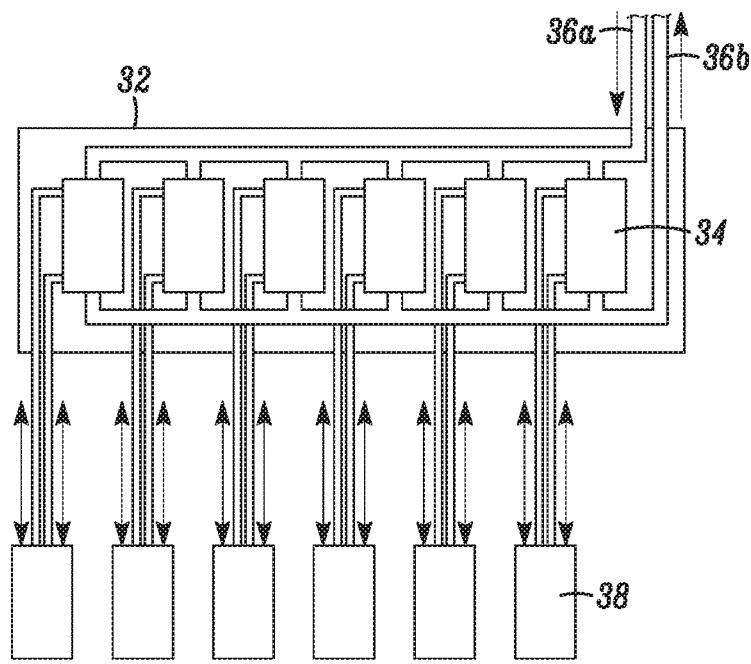
FIG. 1B is a schematic depicting a valve component, according to one embodiment.

Another example of a valve component 32 is provided in FIG. 1B. In this embodiment, the component 32 has six valves 34. The fluid is provided at high pressure through the high pressure supply line 36a and exits the valve component 32 at a low pressure through the low pressure line 36b. In addition, the valves 34 are each coupled to a respective piston assembly 38 as shown. According to one embodiment, such a valve component 30 (also referred to as a "valve system") is sold by Parker Hannifin.

As mentioned above, the fluid actuation systems depicted in FIGS. 1A and 1B can alternatively be a pneumatic system. Returning to FIG. 1A, in this embodiment of a pneumatic system 10, the external pneumatic components 22 are disposed externally to the patient's body. Thus, the pneumatic connection line 20 is connected to the valve component 30 in the medical device 12 and to the external pneumatic components 22 such that the line 20 extends from the interior of the patient's body to the exterior when the device 12 is positioned in the patient's body.

According to one embodiment of a pneumatic system, in place of the pump 26, accumulator 28, and reservoir 24, the external pneumatic component 22 is a pressurized cylinder (not shown). In this embodiment, the return air is emitted into the external environment of the system. One example of a pressurized cylinder is a canister of readily-available carbon dioxide, which is commonly used to insufflate the abdominal cavity during laparoscopic surgery. Alternatively, the external pneumatic components 22 can be any known configuration of any pneumatic components capable of pneumatically powering the piston 16.

Figure 2A:
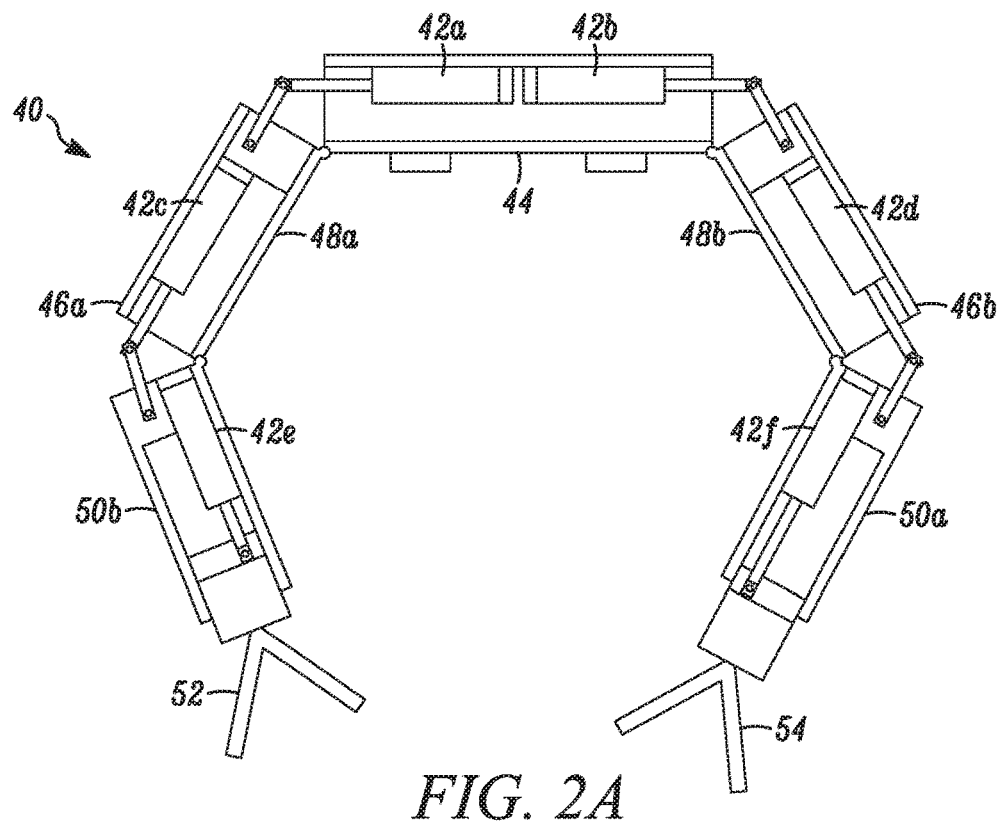
FIG. 2A shows a front view of a medical device having a fluid actuation system, according to one embodiment.
Figure 3:
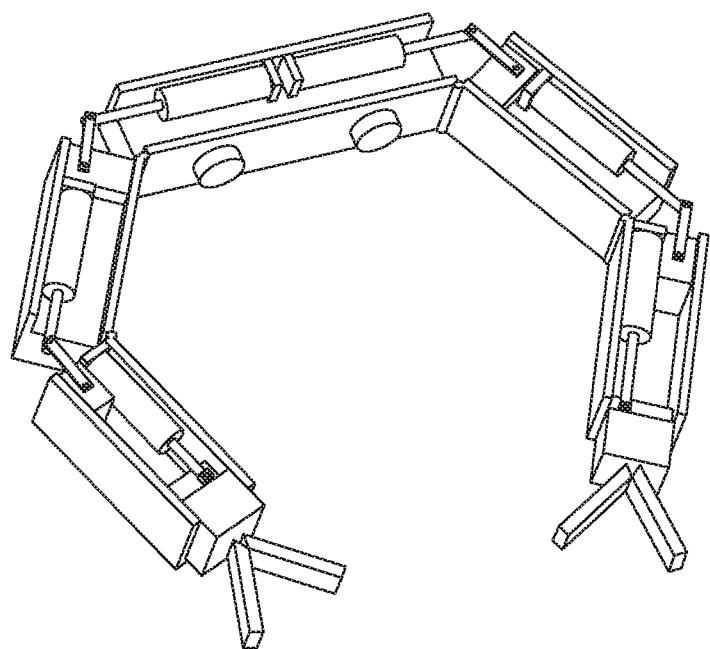
FIG. 3 is a perspective view of a medical device, according to another embodiment.

FIGS. 2A and 3 depict a robotic device 40 with a hydraulic system, according to one embodiment. The device 40 has six piston assemblies 42a, 42b, 42c, 42d, 42e, 42f. Piston assemblies 42a and 42b are disposed within the body 44 of the device 40 and actuate the first links 48a, 48b of the robotic arms 46a, 46b. Piston assemblies 42c, 42d are disposed within the first links 48a, 48b and actuate the second links 50a, 50b. In addition, piston assemblies 42e, 42f are disposed within the second links 50a, 50b and actuate the operational components 52, 54.

Alternatively, the device 40 can have from one to any number of piston assemblies that can be integrated into the robotic device as actuation components. According to one embodiment, a piston is provided for each degree of freedom.

Figure 2B:
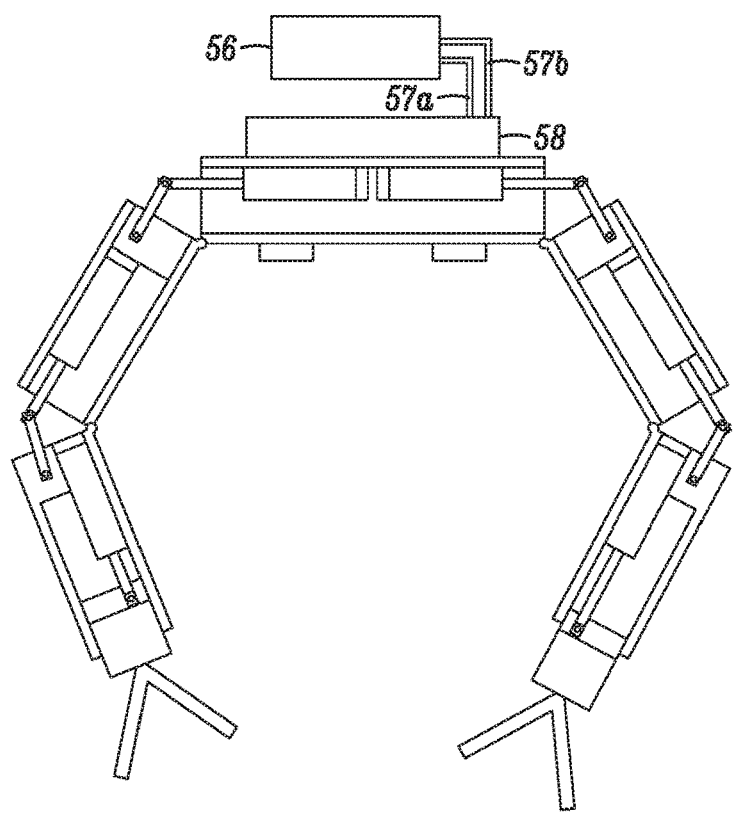
FIG. 2B depicts a front view of a medical device having a fluid actuation system, according to another embodiment.

According to one embodiment as shown in FIG. 2B, the external components of the hydraulic system 56 provide a high pressure supply line 57a to the robotic device and receive a low pressure return line 57b from the device. In a further embodiment, the robotic device has a system of valves or a master valve system 58 that controls the hydraulic fluid flow and directs the fluid as needed to the piston assemblies, such as the assemblies depicted in FIGS. 2A and 3.

Figure 4:
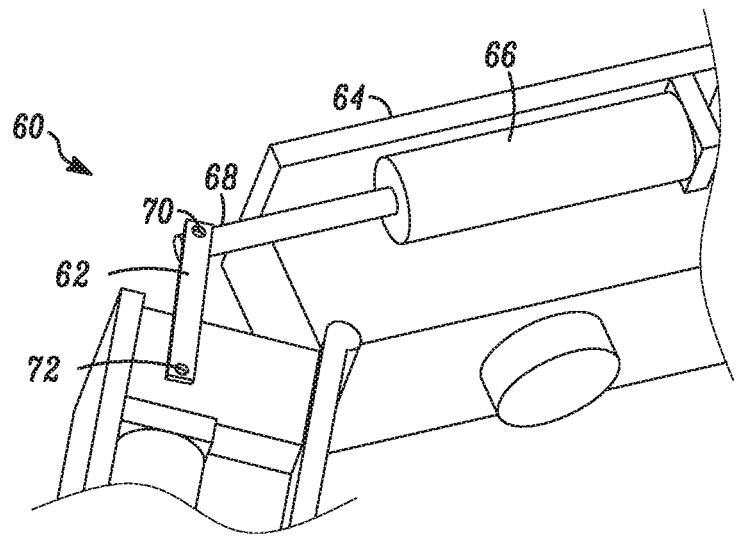
FIG. 4 depicts a perspective view of a medical device joint, according to one embodiment.

FIG. 4 depicts a robotic device joint 60 connecting a link 62 to the robotic body 64, according to one embodiment. The body 64 has a piston assembly 66 in which the piston 68 is coupled to a pin 70 that is coupled in turn to the link 62 at the connection point 72. In one implementation, the link 62 is a first link 62 such that the joint 60 is a joint 60 between a robotic body 64 and a first link 62 (also referred to as a "shoulder joint").

Figure 5:
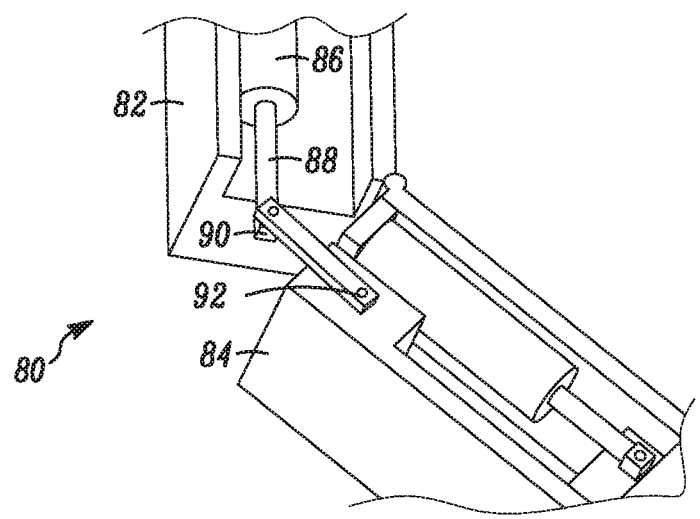
FIG. 5 shows a perspective view of a medical device joint, according to another embodiment.

FIG. 5 depicts a robotic device joint 80 connecting a first link 82 to a second link 84, according to one embodiment. The first link 82 has a piston assembly 86 in which the piston 88 is coupled to a pin 90 that is coupled in turn to the second link 84 at the connection point 92. In one implementation, the joint 80 between the two links 82, 84 is referred to as an "elbow joint."

Figure 6:
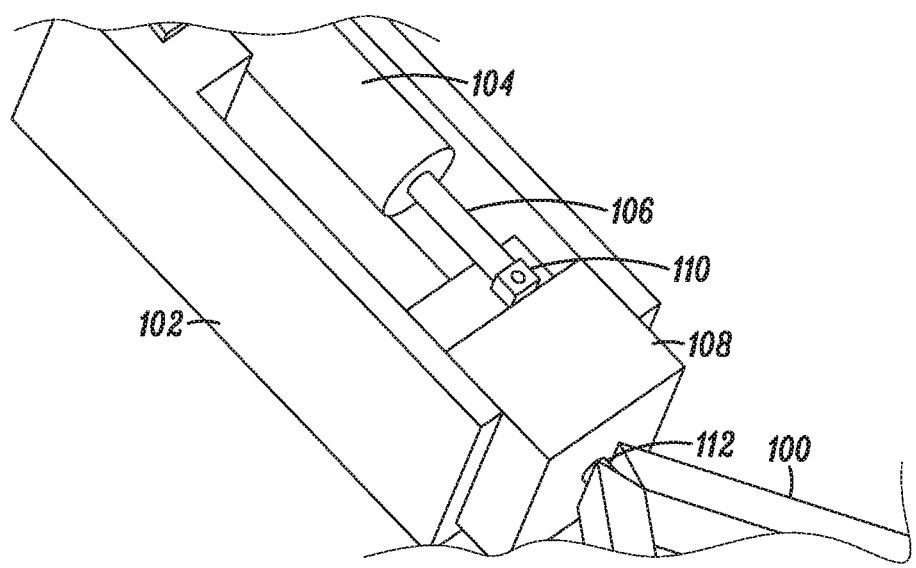
FIG. 6 is a perspective view of an operational component, according to one embodiment.

FIG. 6 depicts an operational component 100 coupled to a robotic arm 102, according to one embodiment. The robotic arm 102 has a piston assembly 104 in which the piston 106 is coupled to a portion of the operational component 100. More specifically, the piston 106 is coupled to a sliding component 108 at a connection point 110, wherein the sliding component is slidably positioned in the arm 102 such that the force created by the piston assembly 104 is translated to the sliding component 110, causing the sliding component 110 to slide back and forth in the arm 102.

The operational component 100 is coupled to the sliding component 110 at joint 112 such that the sliding back and forth of the sliding component 110 causes the operational component 100 to extend and retract relative to the arm 102. This allows for the lengthening and shortening of the reach of the operational component 100 with respect to the arm 102 and the procedural space in which the operational component 100 is operating. Stated in another way, according to one embodiment, this slidable coupling of the sliding component 110 and the arm 102 is considered to be the "wrist" of the arm 102, wherein the sliding of the sliding component 110 back and forth operates to lengthen and shorten the "wrist" in relation to the rest of the arm 102.

In one embodiment, an actuator (not shown) disposed in the sliding component 108 actuates the operational component 100. For example, in the embodiment depicted in FIG. 6 in which the operational component 100 is a set of graspers 100, the actuator actuates the graspers to move between the open and closed positions.

It is understood that a pneumatic system could be incorporated into any of the embodiments and components depicted in FIGS. 2A, 2B, and 3-6 and could operate in generally the same fashion as discussed above. It is further understood that any other type of fluid actuation system could also be implemented in any of these embodiments in generally the same fashion.

In accordance with one implementation, a device having a fluid actuation system such as the various systems disclosed herein could reduce costs associated with the device. That is, the components of the system associated with the device can be integrated into the device at a low cost (in comparison to devices having costly onboard motors, etc.), while the more expensive components can be incorporated into the external components of the system and thus can be re-used for extended periods of time. In another embodiment, the use of a fluid actuation system in a device can provide increased force and/or speed in comparison to internal motors.

In a further alternative embodiment, the device is a "hybrid" that has at least one piston and at least one motor, thereby providing for further flexibility in the configuration of the device and the capability of accomplishing very precise motions. For example, the precise motions could include motions of the wrist such as rotation or extension that might require very precise control for delicate tissue dissection. In such an embodiment, the fluid actuation piston assemblies could be used for purposes of gross and/or quick actuations that require greater power, such as actuation of the shoulder and/or elbow joints, while the motor assemblies could be used for purposes of precise, slower actuations, such as actuation of the wrist or operational component for precise tasks such as dissection. In this context, the fluid actuation assemblies of the shoulder and elbow joints could then subsequently be used for the pulling or cutting motions that require greater power.

Figure 7A:
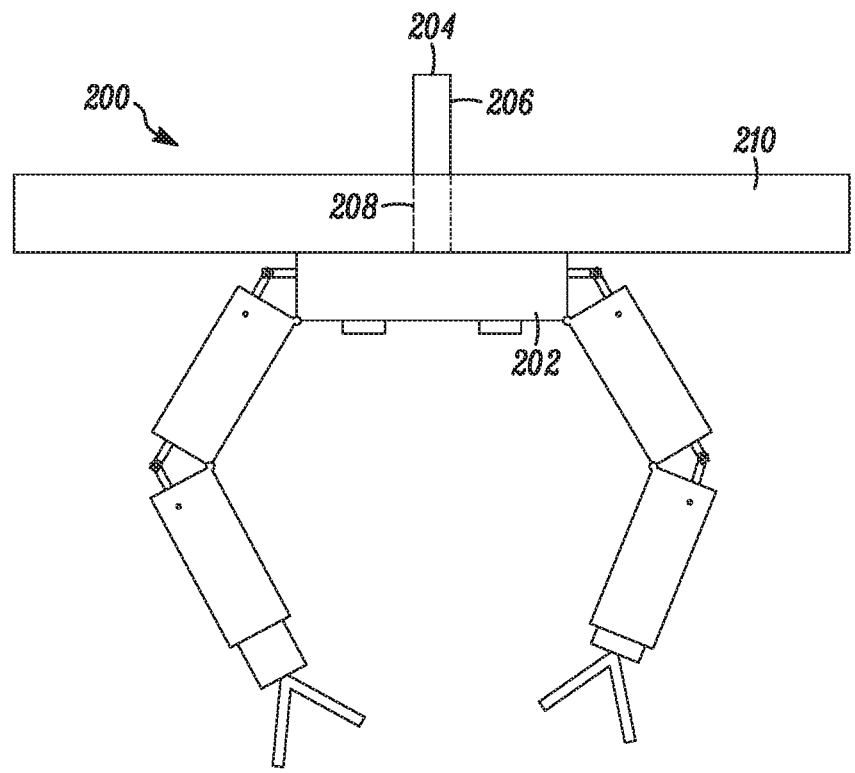
FIG. 7A depicts a front view of a medical device having a drive train system, according to one embodiment.

In addition to the fluid actuation systems described above, yet another actuation system that can be implemented with the various medical devices disclosed or incorporated herein is a drive train system. One exemplary implementation of a drive train system is shown in FIG. 7A, which depicts a robotic device 202 mechanically powered or actuated with a drive train system 200. The system 200 has a drive component 204 that is coupled to the robotic device 202 and thereby provides mechanical force to the device 202.

Figure 7B:
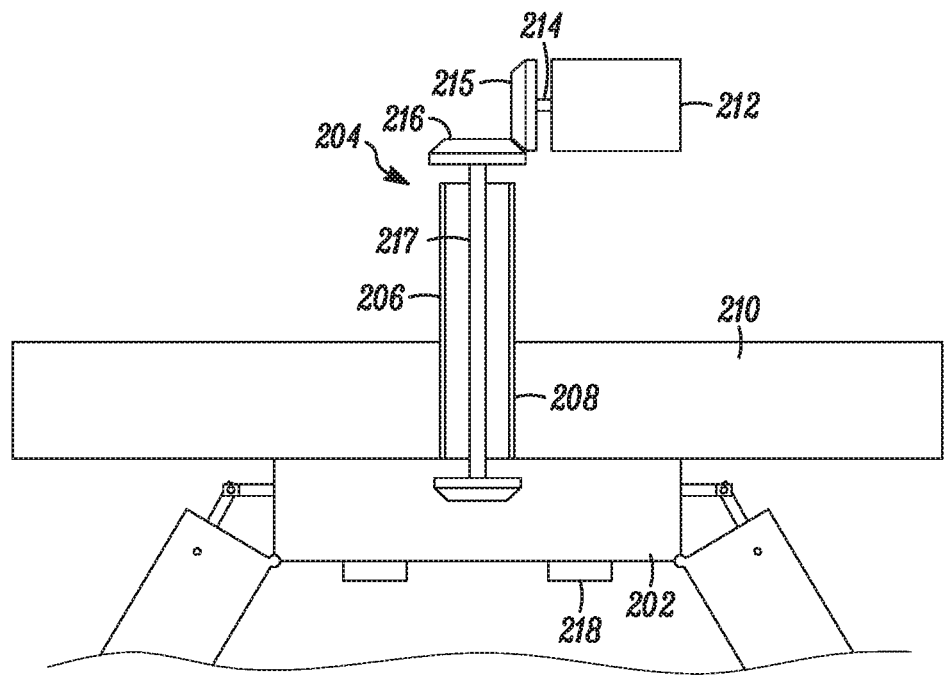
FIG. 7B shows a front view of a medical device having a drive train system, according to another embodiment.

In one embodiment as shown in FIG. 7B, the drive component 204 includes a series of axles and couplers that are connected to each other and to an actuation component 212 (which, according to one implementation, can be a drive motor 212) and ultimately are connected to the device 202. More specifically, the drive component 204 includes the drive shaft 214, the first coupling component 215, the second coupling component 216, the connecting shaft 217, and the third coupling component 218. According to one embodiment, the first, second, and third coupling components 215, 216, 218 are coupleable gears. In operation, the actuation component 212 depicted in FIG. 7B powers the drive component 204 by actuating the drive shaft 214. The rotation of drive shaft 214 powers the rotation of the connecting shaft 217 via the first and second coupleable gears 215, 216. The power is then transferred to the medical device 202 via the third gear 218.

Alternatively, the drive component 204 is a flexible rod that is capable of transferring rotational power to the device 202. In a further embodiment, the drive component 204 is any known drive component capable of transferring power to a robotic device 202.

As shown in FIGS. 7A and 7B, this particular embodiment relates to a drive component 204 that is positioned inside a needle, port, or other kind of insertion component 206 that is connected to a device 202 positioned inside the patient's body. Alternatively, the insertion component 206 is an opening or channel that provides for access or connection to the device 202 inside the patient's body. More specifically, in the embodiment depicted in FIG. 7, the insertion component 206 is a trocar-like port 206 that is inserted through an incision 208 in the patient, such as an incision 208 through the abdominal wall 210. The drive component 204 is then positioned within the port 206 and coupled to the device 202 positioned in the patient's body cavity.

As described above, the drive component 204 can be a rotary shaft 204 that supplies rotational actuation to the device 202. In one exemplary implementation, the shaft 204 has a series of clutches (not shown) that transfer the actuation to the piston assemblies or other translation assemblies for actuation of the joints and other actuable components.

The miniature clutches are common components that are available commercially from Small Parts, Inc., located in Miami Lakes, Fla. In one embodiment, the clutches are operated hydraulically. Alternatively, the clutches are operated electrically or by any other known method.

In a further alternative implementation, the drive component 204 winds one or more onboard tensionable springs that can then be used to provide power to the end effectors or other drivable/driven components in the device through a clutch system.

Alternatively, the rotary shaft 204 is a flexible rod 204. In this embodiment, the insertion component 206 does not necessarily need to be straight. In one example, the insertion component 206 is inserted through the esophagus of the patient and into the abdominal cavity through an incision in the stomach wall. The inner flexible rod 204 is positioned within the insertion component 206 and coupled to the robotic device 202. In this example, the flexible rod 204 is rotated to provide rotational actuation to the robotic device 202.

One component that can be used in conjunction with any fluid actuation or drive train actuation system such as those systems described above is a reversibly lockable tube. As used herein, "reversibly lockable tube" is intended to mean any tubular component that can be switched, adjusted, or otherwise changed between a flexible configuration and a locked configuration (in which "locked" is intended to encompass any level of substantial rigidity). This adjustability between flexible and rigid configurations shall also be referred to herein as the "reversibly lockable" feature. Please note that the term "tube" as used herein is intended to encompass any tubular or hose-like component that provides access to various cavities of a patient's body for medical procedure devices and/or connection to such devices positioned in the patient's body.

Figure 8:
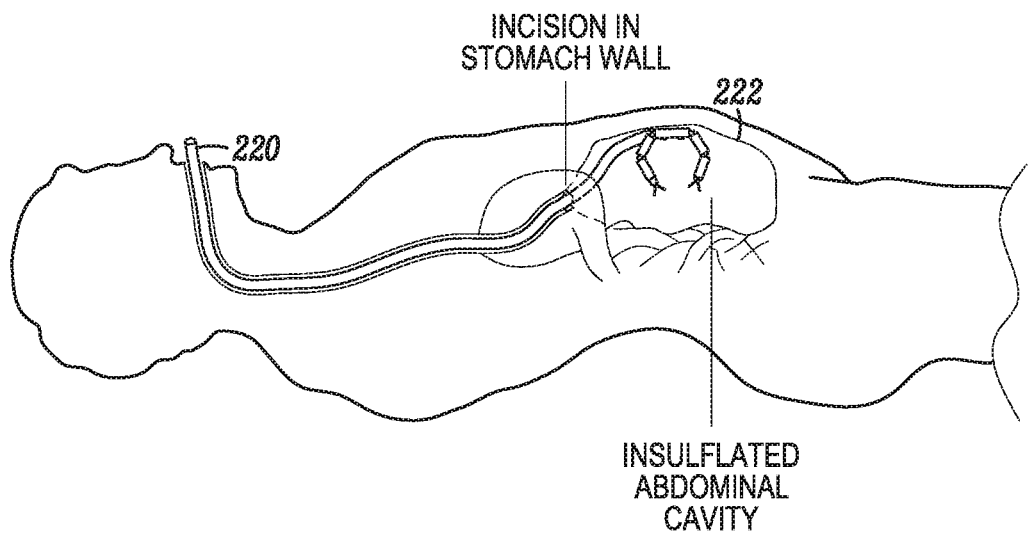
FIG. 8 is a cutaway view of a reversibly lockable tube positioned in a target body cavity of a patient, according to one embodiment.

FIG. 8 provides one exemplary depiction of an embodiment of a reversibly lockable tube 220 coupled to a robotic device 222 that is positioned in the target body cavity of the patient. As discussed above, one embodiment of the tube 220 can be adjusted between a flexible configuration and a rigid or "locked" configuration. In use, such components as a hydraulic or pneumatic actuation system as described above can be disposed within the tube 220, along with any other components that connect a robotic device disposed within the patient's body with components positioned externally to the patient's body. More specifically, the tube 220 is maintained in its flexible configuration while the tube 220 is being positioned through an orifice into a patient's body such as through the mouth and esophagus of the patient as depicted in FIG. 8. Once the tube 220 has been positioned, the tube 220 can be adjusted into the locked configuration during operation of the device 222. The operation of the various lockable tube embodiments disclosed herein will be described in further detail below.

FIGS. 10 and 11 depict a reversibly lockable tube 240 according to one embodiment that is made up of multiple modular tube components (also referred to herein as "links").

Figure 9A:
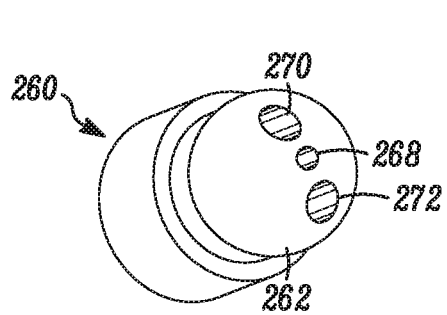
FIG. 9A depicts a perspective view of a modular tube component, according to one embodiment.
Figure 9B:
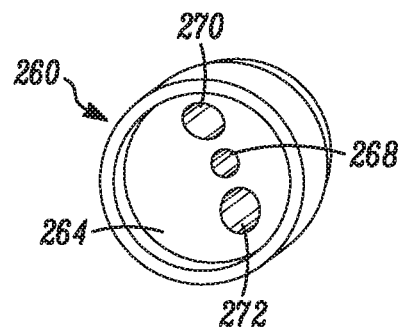
FIG. 9B shows another perspective view of the modular tube component of FIG. 9A.

One example of modular tube components 260 (such as those used in the tube 240 shown in FIGS. 10 and 11) is depicted in FIGS. 9A and 9B. FIG. 9A depicts the male end 262 (or "protrusion"), while FIG. 9B depicts the female end 264. As shown in FIG. 9A, the male end 262 is a convex protrusion. Alternatively, the male end 262 can be any form of protrusion that mates with the female end 264. As shown in FIG. 9B, the female end 264 is a concave formation. Alternatively, the female end 264 can take any form or configuration that mates with the male end 262.

As shown in FIGS. 9A and 9B, each modular component 260 has at least one hole 268 (also referred to herein as a "channel") defined through the component 260. As depicted, the component 260 has three channels 268, 270, 272. According to one embodiment, the channels 268, 270, 272 are configured to receive and/or allow the passage of any cables or tubes that are to be inserted through or positioned within the reversibly lockable tube 240, such as those shown in FIGS. 10 and 11. In accordance with one implementation, the center channel 268 is configured to receive a rigidity cable 242, best shown in FIGS. 10 and 11. The rigidity cable 242 is used to convert or adjust the tube 240 into the rigid configuration or phase. Any additional channels, such as channels 270, 272, are configured to receive electrical connection components, hydraulic or pneumatic tubes, or any other elongate members that require insertion into the target cavity or connection to a robotic device positioned in the target cavity.

Figure 12:
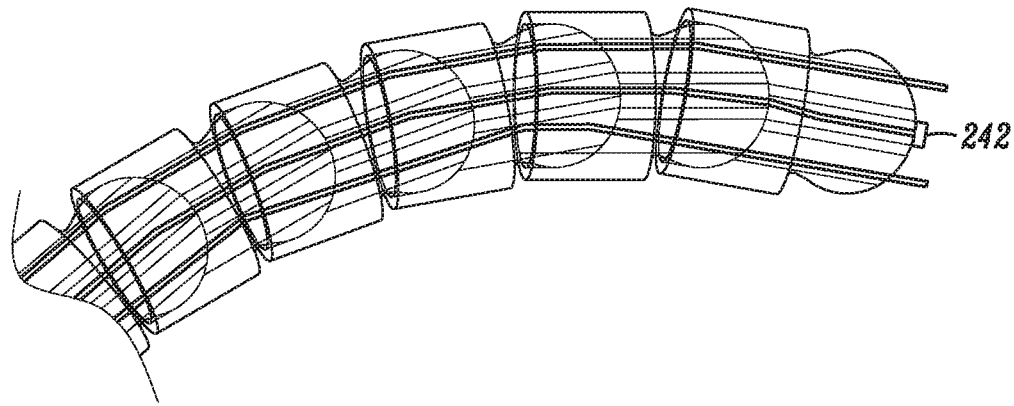
FIG. 12 shows a perspective view of a reversibly lockable tube, according to another embodiment.

According to one embodiment as best shown in FIGS. 10, 11, and 12, the rigidity cable 242 operates in the following manner to adjust or convert the tube 240 from the flexible configuration to the rigid configuration. In the flexible state as shown in FIG. 11, the cable 242 is allowed to be loose and thus the modular components 246 are not being urged against each other into a tight configuration. According to one embodiment, each modular component 246 can move about 20 degrees relative to the adjacent components 246 in the flexible state. When it is desirable to adjust or transform the tube 240 from the flexible state to the rigid state, the cable 242 is pulled or otherwise urged at its proximal end 248 in a direction away from the tube 240. This causes the cable end 244 to contact the distal modular component 250 and begin urging that component 250 toward the other components of the tube 240. Ultimately, this urges the modular components 246 into a tight configuration of the components 246 in which each of the components 246 is stacked tightly, or is otherwise in close contact, with the other components 246, thereby resulting in a substantially rigid configuration of the tube 240.

Figure 13:
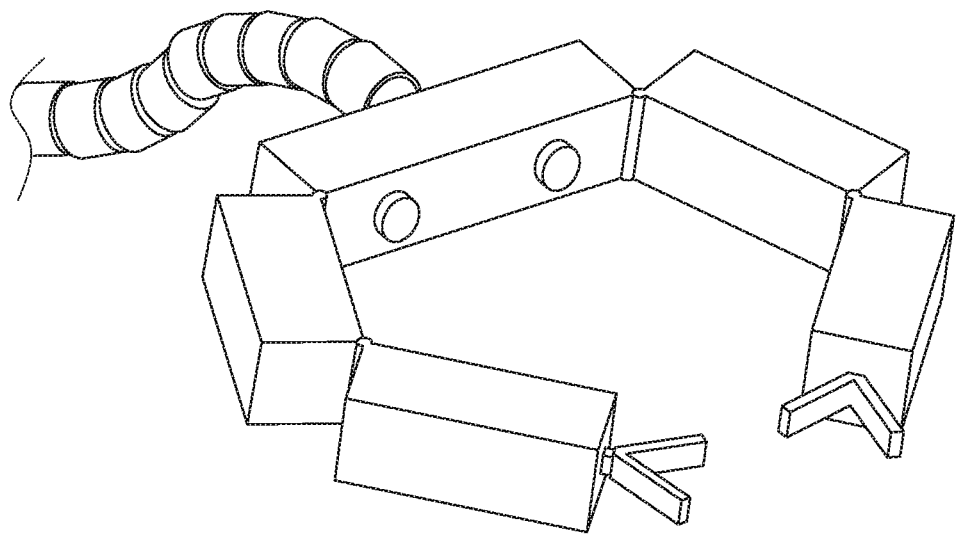
FIG. 13 is a perspective view of a reversibly lockable tube, according to yet another embodiment.

In use, the tube (such as tubes 220 or 240, for example) is placed in its flexible configuration or state for insertion of the robotic device into the patient's body. Once the device has been positioned as desired by the user (such as the positioning of the device 222 and tube 220 depicted in FIG. 8 or alternatively as shown in FIG. 13), the tube is then adjusted or converted or otherwise placed into its rigid configuration or phase. This rigidity can assist in maintaining the geometric or physical shape and/or positioning of the tube in relation to the patient and resist against the straightening force of the hydraulic, pneumatic, or physical force being applied through the connections between the device and the external components of the hydraulic, pneumatic, or drive train systems, respectively, as known in the art or as described above. Thus, the tube can assist in maintaining the stability of the robotic device during use. Alternatively, the rigidity can assist with maintaining the geometric or physical shape and/or positioning of the tube for any reason that may benefit the operation of the medical device or the medical procedure generally.

In addition to the fluid actuation system and drive train embodiments discussed above, yet another actuation component that can be incorporated into or used with any of the medical devices disclosed or otherwise described herein is a motorless actuation system or component.

Figure 14A:
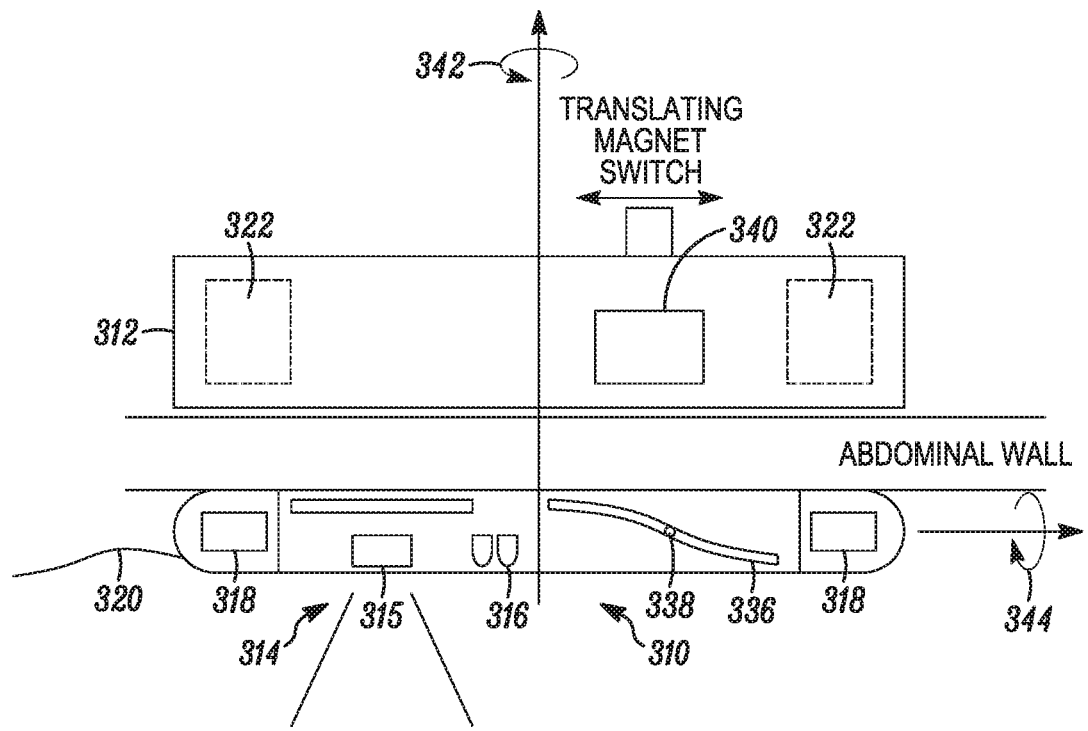
FIG. 14A depicts a front view of a medical device having a motorless actuation component, according to one embodiment.
Figure 14B:
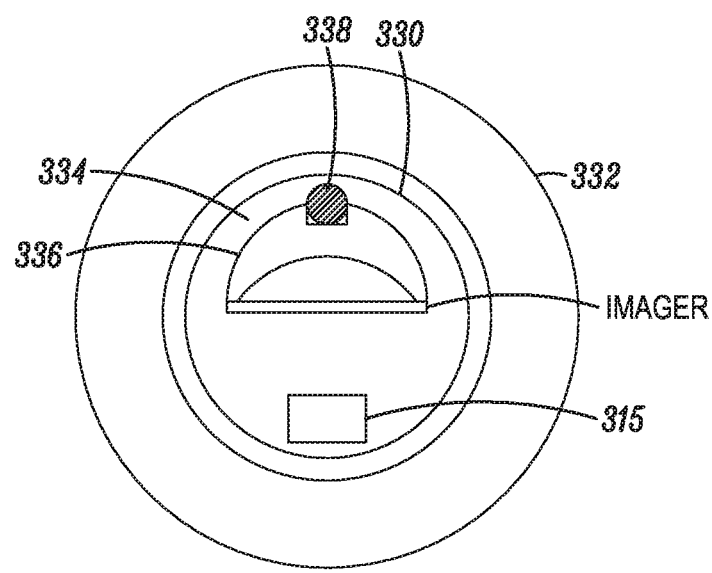
FIG. 14B shows a side view of the medical device of FIG. 14A.

FIGS. 14A and 14B depict one embodiment of a motorless actuation component. More specifically, FIGS. 14A and 14B depict a robotic camera device 310, according to one embodiment, in which the robotic device 310 is disposed within the abdominal cavity of a patient, and a magnetic handle 312 is disposed at a location external to the patient. The handle 312 operates to hold the device 310 inside the abdominal cavity against the peritoneum (abdominal wall) via magnetic forces.

It is understood that this embodiment is similar to the embodiments disclosed in U.S. patent application Ser. No. 11/766,720, filed on Jun. 21, 2007, and U.S. patent application Ser. No. 11/766,683, filed on Jun. 21, 2007, both of which were incorporated herein above. It is further understood that any of the instant motorless actuation component embodiments can be incorporated into any of the embodiments disclosed in those co-pending applications.

In the implementation shown in FIGS. 14A and 14B, the device 310 is cylindrical and includes an imaging component 314, a lighting component 316, magnets 318 at each end of the device, and a wired connection component 320 (also referred to herein as a "wire tether"). The magnets 318 are magnetically coupleable with magnets 322 on the handle 312 such that the device 310 is urged toward and held against the body cavity wall. In one embodiment, the magnets 318 are configured to ensure that the imaging component 314 is positioned to capture a view of the body cavity or the target area of interest.

It is understood that the magnets 318 in the device 310 and those magnets 322 in the handle 312 can be positioned in any configuration and include any number of magnets as disclosed in the U.S. patent application Ser. Nos. 11/766,720 and 11/766,683, incorporated herein.

It is further understood that, in one embodiment, the magnetic handle 312, also referred to herein as an "external magnet," is in the shape of a handle. Alternatively, the handle 312 is intended to encompass any magnetic component that is magnetically coupleable with any robotic device as described herein such that the magnetic component can be used to position, operate, or control the device.

In one embodiment as described in the incorporated references above, the handle 312 can be rotated as shown by arrow 342 to allow a tilting functionality for the imaging component. Further, the device can also provide for a panning functionality via rotation of the imaging component as shown by arrow 344, as described in further detail below.

In use, the device 310 can be moved within the patient's body to any desired position by moving the handle 312 outside the body. Alternatively, the device 310 can be positioned, operated, or controlled anywhere in a patient's body at least in part by the magnetic handle 312 positioned outside the body in any fashion described in the references incorporated above.

According to one implementation, the robotic device 310 shown in FIGS. 14A and 14B has two portions: an inner portion 330 and an outer portion 332, as best shown in FIG. 14B. The inner portion 330, according to one embodiment, is a cylindrically shaped inner body 330, and the outer portion 332 is an outer sleeve 332 configured to be rotatably disposed over the inner body 330. In such an embodiment, the imaging component 314 and lens 315 can be panned by rotating the inner body 330 with respect to the sleeve 332, causing the lens 315 to rotate in a fashion similar to that depicted by the arrow 344. In accordance with one implementation, the inner body 330 is coupled to the outer sleeve 332 with a set of bearings (not shown).

In one implementation, the actuation component 334 that rotates the inner portion 330 relative to the outer portion 332 is a motorless actuation component. That is, the actuation component is not a motor or a motorized component of any kind. For example, the actuation component 334 as shown in FIGS. 14A and 14B includes a race 336 and ball 338. In this embodiment, a magnet 340 external to the patient is used to urge the ball 338 along the race 336. In such an embodiment, the magnet 340 can be coupled with the magnetic handle 312 described here as shown in FIG. 14A. In one embodiment, the race 336 is helical and the ball 338 is steel. In a race and ball implementation, as the ball 338 moves along the race channel 336, the inner body 330 rotates relative to the outer sleeve 332. In another embodiment, the ball 338 is magnetic and moves along a race 336.

Figure 15:
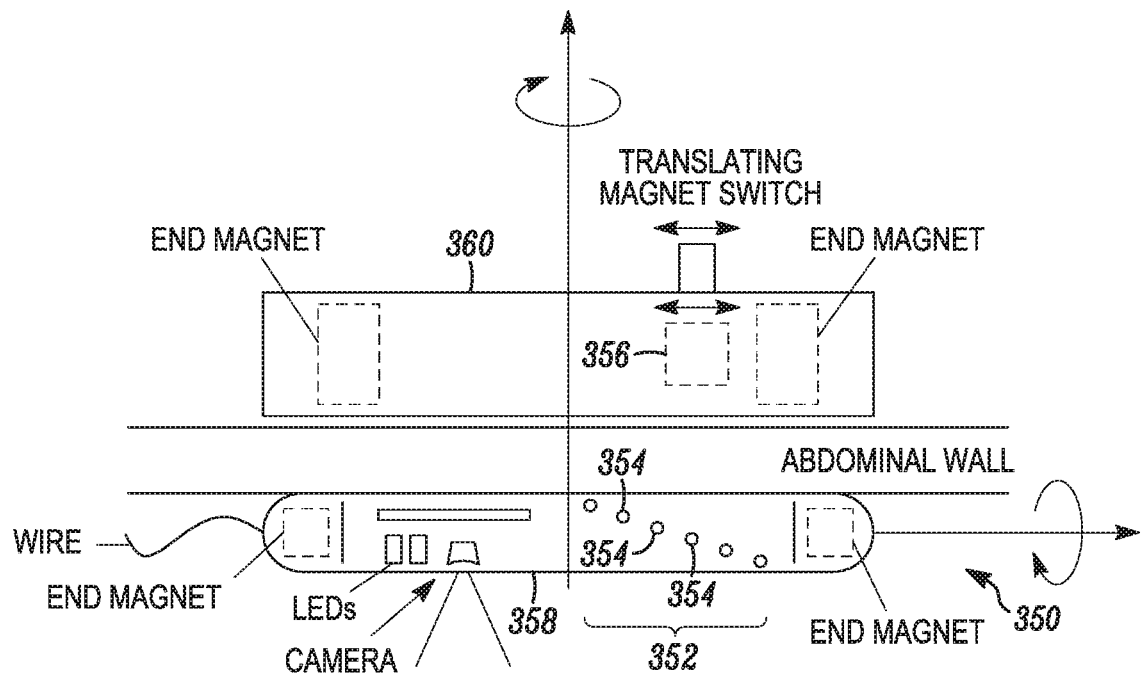
FIG. 15 is a front view of a medical device having a motorless actuation component, according to another embodiment.

FIG. 15 depicts an alternative embodiment of a motorless actuation component in which the actuation component 352 has multiple magnets 354 that are disposed in or on the robotic device 350. In this embodiment, the magnets 354 are placed in a helical pattern in the inner cylinder (not shown) so that as the external magnet 356 is translated, the inner body rotates relative to the outer sleeve 358 as the inner body magnet 354 in closest proximity to the external magnet 356 is urged toward the external magnet 356. In another embodiment, a series of electromagnets in the handle 360 can be actuated in order to move the effective magnetic field along the handle 360.

In yet another alternative embodiment, the ball can be urged along the race by other means. For example, the device can have a cable or wire connected to it and also connected to an external handle. Actuation of this cable urges the ball along the race, thereby resulting in a panning motion of the inner body relative to the outer sleeve. In one embodiment, the cable is attached or operably coupled in some fashion to the ball so that actuation of the cable urges the ball along the race.

In a further alternative, the motorless actuation component does not include a ball and race, but instead has a drum. In this embodiment, a cable such as that described above is attached to the drum so that actuation of the cable urges the drum to rotate. This rotation of the drum causes rotational actuation in the medical device. Alternatively, any known method of transitioning translation motion into rotary motion could be used. Further, it is understood that any known motorless actuation component can be incorporated into any of the medical devices described herein or incorporated by reference herein.

Various mechanical arm embodiments are provided herein that can be incorporated into any number of different kinds of medical devices. The medical device arm configurations disclosed herein provide for various arm embodiments having two degrees of freedom—both (1) axial movement (extension and retraction of a portion of the arm along the longitudinal axis of the arm), and (2) rotational movement around the axis of the arm. These configurations provide for the two degrees of freedom while maintaining a relatively small or compact structure in comparison to prior art configurations.

It is understood that the arm embodiments disclosed herein can be utilized in any type of medical device, including those devices in which a compact or smaller size is desirable, such as devices for procedures to be performed within a patient. For example, the arm embodiments could be incorporated into various robotic medical devices, including in vivo robotic devices such as robotic devices positionable on or near an interior cavity wall of a patient, mobile robotic devices, or robotic visualization and control systems.

An "in vivo device" as used herein is any device that can be positioned, operated, or controlled at least in part by a user while being positioned within a body cavity of a patient, including any device that is positioned substantially against or adjacent to a wall of a body cavity of a patient, and further including any such device that is internally actuated (having no external source of motive force). As used herein, the terms "robot," and "robotic device" shall refer to any device that can perform a task either in response to a command or automatically. Further, the arm embodiments could be incorporated into various robotic medical device systems that are actuated externally, such as those available from Apollo Endosurgery, Inc., Hansen Medical, Inc., Intuitive Surgical, Inc., and other similar systems.

Figure 16:
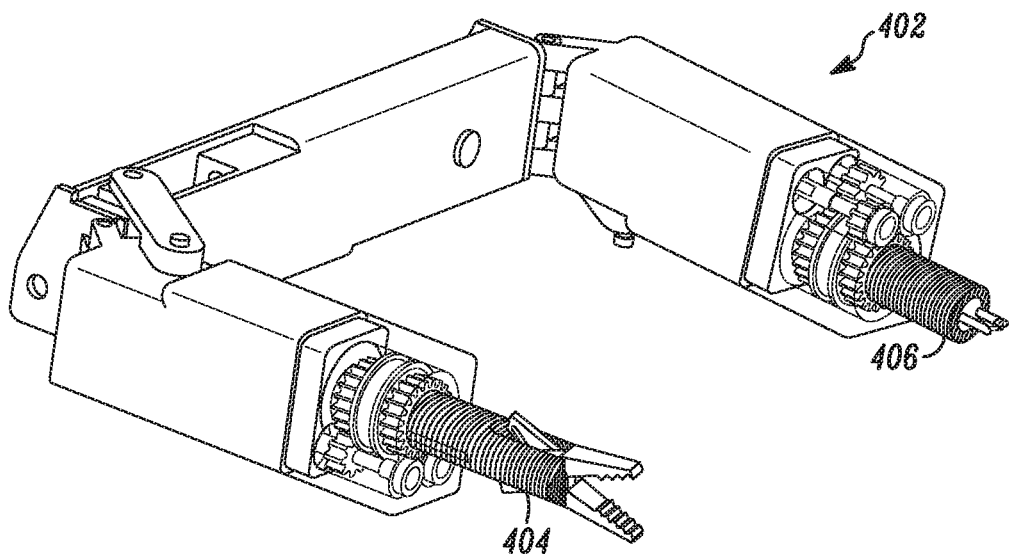
FIG. 16 depicts a perspective view of a medical device having an arm component, according to one embodiment.

According to one embodiment as depicted in FIG. 16, one arm embodiment is incorporated into an in vivo medical device 402 as shown. The device 402 has two robotic arms 404, 406 that can be configured according to any embodiment described herein.

Figure 17A:
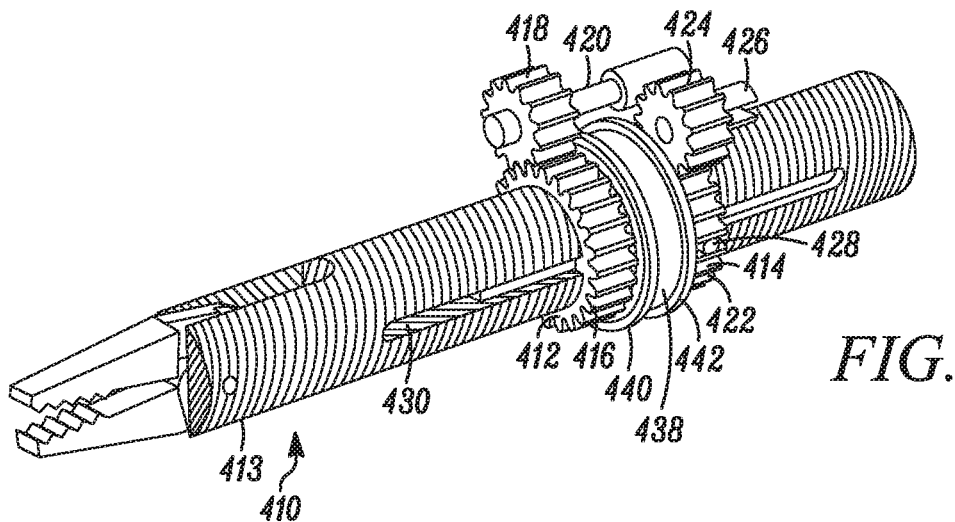
FIG. 17A shows a perspective view of an arm component, according to one embodiment.
Figure 17B:
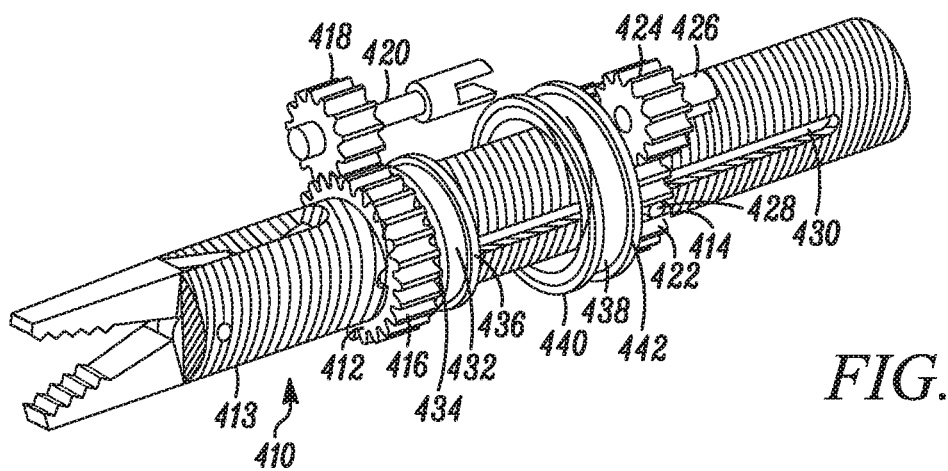
FIG. 17B is a perspective exploded view of the arm component of FIG. 17A.

FIGS. 17*a* and 17*b* depict a device arm 410, according to one embodiment. The arm 410 has two gears: (1) a distal gear 412 that provides for extension and retraction of the arm 410, and (2) a proximal gear 414 that provides for rotation of the arm 410.

The distal gear 412 has gear teeth 416 on its outer surface and further is threaded on its inner surface (not shown). The gear teeth 416 mate or couple with gear teeth 418 on a drive gear 420, which is coupled to an actuator (not shown). In one embodiment, the actuator is a Permanent Magnet Direct Current ("PMDC") motor. Thus, the distal gear 412 is driven by the actuator.

The threading on the inner surface of the distal gear 412 mates or couples with the threading 413 on the outer surface of the arm 410 such that when the distal gear 412 is driven by the actuator, the gear 412 rotates and the coupling of the threads on the inner surface of the gear 412 with the threads 413 on the arm 410 causes the arm 410 to extend or retract depending on which direction the gear 412 turns.

The proximal gear 414 has gear teeth 422 on its outer surface that mate or couple with gear teeth 424 on a drive gear 426, which is coupled to an actuator (not shown). The gear 414 also has a pin 428 disposed within the gear 414 that extends through the gear 414 and further through a slot 430 in the arm 410. Thus, when the proximal gear 414 turns, the pin 428 causes the arm 410 to turn as well.

The distal 412 and proximal 414 gears interface or interact at the bearing surfaces. More specifically, the distal gear 412 has a bearing surface 432 (best shown in FIG. 17*b*) having two bushings 434, 436 disposed or positioned on the outer surface of the bearing surface 432. Similarly, the proximal gear 414 has a bearing surface 438 having two bushings 440, 442. The bearing surface 432 has a smaller diameter than, and is disposed within, the bearing surface 438 such that the inner surface of bearing surface 438 is in contact with the two bushings 434, 436. As such, the bearing surfaces 432, 438 contact each other and rotate in relation to one another at the two bushings 434, 436. Further, the two bushings 440, 442 disposed on the outer surface of the bearing surface 438 typically contact the external gear housing or other type of housing (not shown).

In an alternative embodiment, gear pairs 418, 412 and 424, 422 as depicted in FIGS. 17A and 17B are replaced with round wheel pairs in which each wheel is configured to be in contact with the other wheel in the pair. In such an embodiment, each wheel has a coating or other surface component that provides for sufficient friction when the wheels are in contact to transmit rotational energy between the two wheels. According to one embodiment, the coating is a thin rubber coating. Alternatively, the coating or surface can be any known coating or surface that provide sufficient friction to allow transmission of rotational energy. This friction drive system allows the gearing components to be reduced in size because of the elimination of the gear teeth.

In a further embodiment, the gears can also be replaced with a series of cables and drums that are used to actuate the arm. In this pulley system embodiment, the actuator that drives the cables can be located in another portion of the robot, while a series of drums are disposed on the arms. The cabling connects the drums with the actuator (such as a motor). This embodiment allows the actuators, drums, and arm components to be configured in a variety of different orientations while still providing sufficient actuation forces and speed to the arm end effectors.

Figure 18:
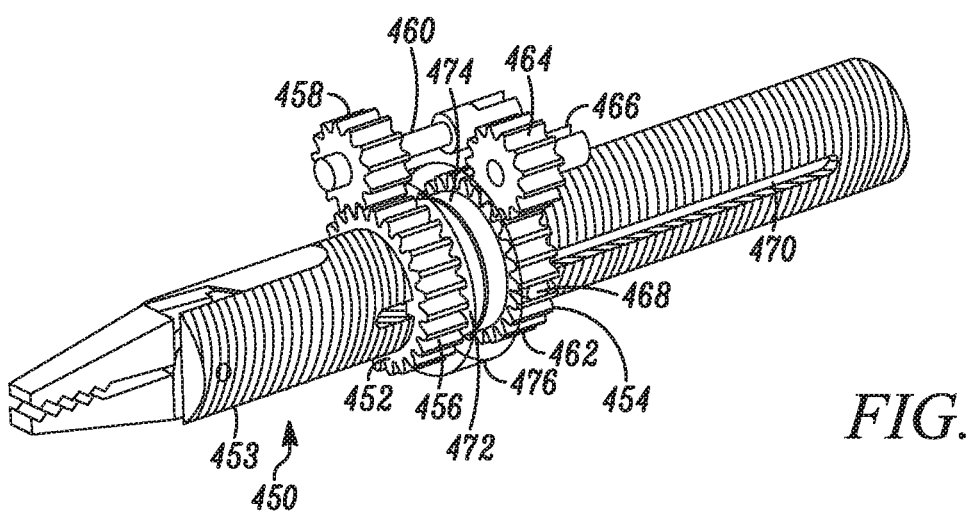
FIG. 18 depicts a perspective view of an arm component, according to another embodiment.

FIG. 18 depicts another device arm 450, according to an alternative embodiment. The arm 450 has a distal gear 452 and a proximal gear 454.

The distal gear 452 has gear teeth 456 and is threaded on its inner surface (not shown). The gear teeth 456 mate or couple with gear teeth 458 on a drive gear 460, which is coupled to an actuator (not shown). As with the previous embodiment, the threading on the inner surface of the distal gear 452 mates or couples with the threading (453) on the outer surface of the arm 450 such that when the distal gear 452 is driven by the actuator, the gear 452 rotates and the coupling of the threads on the inner surface of the gear 452 with the threads 453 on the arm 450 causes the arm 450 to extend or retract depending on which direction the gear 452 turns.

Similarly, the proximal gear 454 has gear teeth 462 on its outer surface that mate or couple with gear teeth 464 on a drive gear 466, which is coupled to an actuator (not shown). The gear 454 also has a pin 468 disposed within the gear 454 that extends through the gear 454 and further through a slot 470 in the arm 450. Thus, when the proximal gear 454 turns, the pin 468 causes the arm 450 to turn as well.

The bearing surfaces in this embodiment depicted in FIG. 18 differ from those in the prior embodiment. That is, the distal gear 452 has a bearing surface 472 that is adjacent to and in contact with a bearing surface 474 of the proximal gear 454. Thus, the gears 452, 454 rotate in relation to each other at the bearing surfaces 472, 474. In addition, the two bearing surfaces 472, 474 typically contact or are disposed within an external gear housing 476.

Although the present invention has been described with reference to preferred embodiments, persons skilled in the art will recognize that changes may be made in form and detail without departing from the spirit and scope of the invention.

One end effector or operational component that can be used with any of the procedural devices disclosed herein is a winch system. Generally, the devices or systems discussed herein are configured to be inserted into or positioned in a patient's body, such as a body cavity, for example. Alternatively, the winch systems and devices disclosed herein can be used with any medical or procedural device.

Figure 19A:
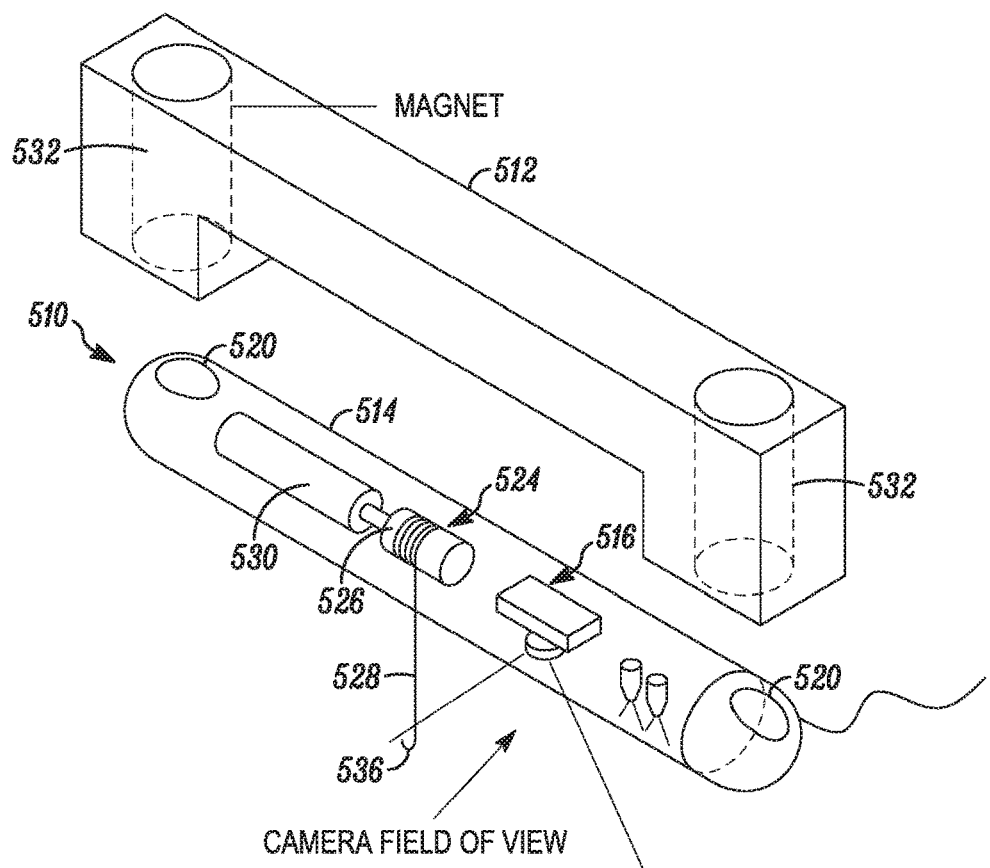
FIG. 19A shows a perspective view of a medical device having a winch component, according to one embodiment.
Figure 19B:
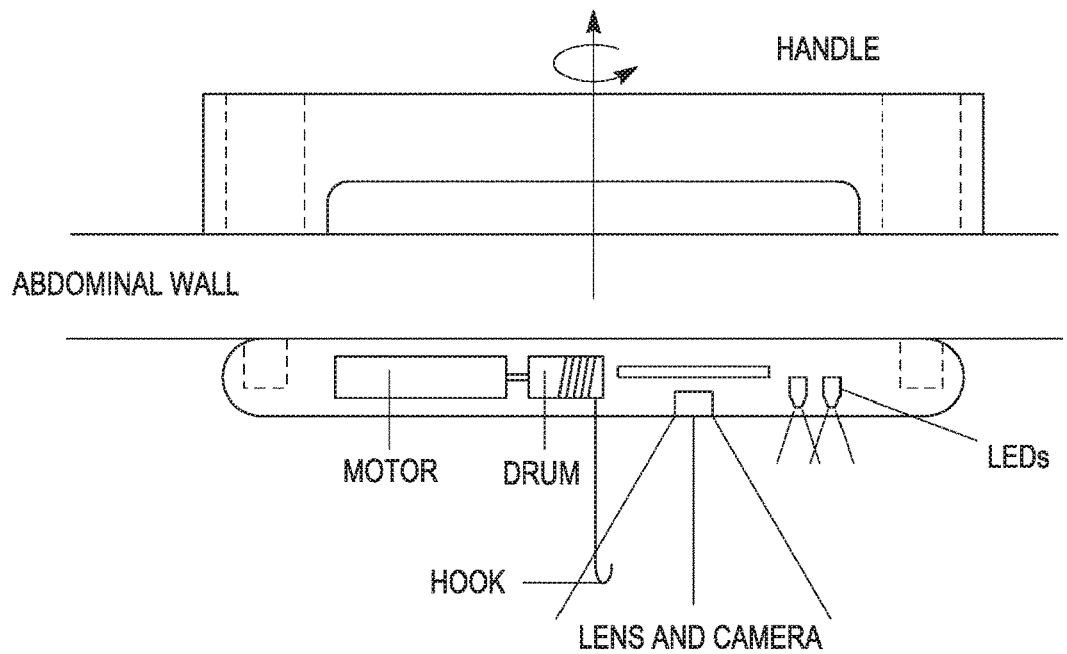
FIG. 19B is a front view of the medical device having the winch component of FIG. 19A.

One embodiment of a medical device having a winch component is set forth in FIGS. 19A and 19B. The medical device 510 is an in vivo robotic device 510 that can be positioned within a cavity of a patient, and further has a magnetic handle 512 that can be disposed at a location external to the patient. In this embodiment, the handle 512 operates to hold the device 510 inside the abdominal cavity against the peritoneum (abdominal wall) via magnetic forces. Alternatively, any known method or component for holding the device 510 against the wall could be used. For example, in one embodiment, the robot 510 could be held against the wall using hooks or clamps. In a further alternative, the winch systems disclosed herein can be used with any known medical devices, including—but not limited to—in vivo devices with arms or wheels.

In the implementation depicted in FIGS. 19A and 19B, the device 510 has a winch component 524 and a motor 530 to actuate the winch 524. In this embodiment, the winch component 524 includes a drum 526 and a winch tether 528. The drum 526 operates to wind and unwind the winch tether 528.

In accordance with the depicted embodiment, the device 510 has magnets 520 that are magnetically coupleable with magnets 532 on the handle 512 such that the device 510 is urged toward and held against the body cavity wall. The device 510, the handle 512, and the magnets 520, 532 can be configured and/or operated in the same fashion as described in U.S. application Ser. No. 11/766,720, filed on Jun. 21, 2007 and entitled "Magnetically Coupleable Robotic Devices and Related Methods," which is incorporated by reference above. In one embodiment, it is understood that the magnets 520 are configured not only to ensure that the imaging component 516 is positioned to capture a view of the body cavity or the target area of interest for securing the winch 524, but are also configured to provide a magnetic coupling that is strong enough to maintain the device 510 in a stable and substantially fixed position such that the winch component 524 can be operated as desired and as described herein.

According to the exemplary embodiment in FIGS. 19A and 19B, the actuation component 530 is a motor 530 that provides force for rotating the drum 526. In this embodiment, the motor 530 is a 6 mm brushed motor that turns a planetary gear, which revolves around a stationary sun gear, thereby causing the drum 526 to rotate inside the body 514. Alternatively, a clutch (not shown) can be used to provide both (1) panning motion of a camera 516 along the axis of the body 514, and (2) winch actuation using a single motor. In a further alternative, an exterior drive train can be used to actuate the winch 524. It is understood that any known actuation component that can be used with medical devices can be used with the winch components or systems disclosed herein.

In one embodiment, the winch tether 528 is made from suture material. In another embodiment, it is metallic cabling. Alternatively, any known material for use in a medical winch tether can be used.

Figure 20:
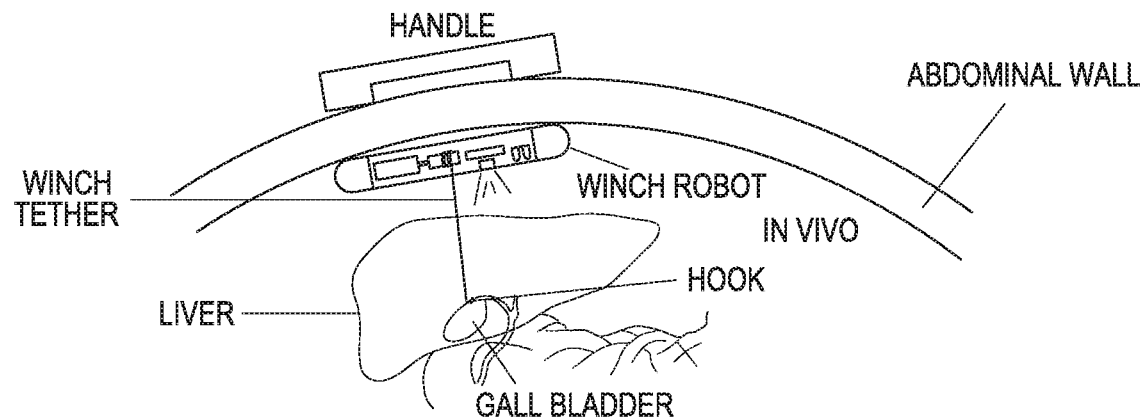
FIG. 20 depicts a cutaway view of a medical device utilizing a winch component during a procedure in a patient, according to one embodiment.

In one embodiment, various operational components or end effectors can be attached to the end of the winch tether. In one embodiment, the end of the winch tether 528 is attached to a hook 536, as depicted in the embodiment of FIGS. 19A and 19B. Such a hook is depicted in use in FIG. 20. Alternatively, the end effector (also referred to as an "operational component") of the tether can be a clamp or loop. In a further alternative, any known operational component, including any known component for attaching to tissue, can be used.

Figure 21:
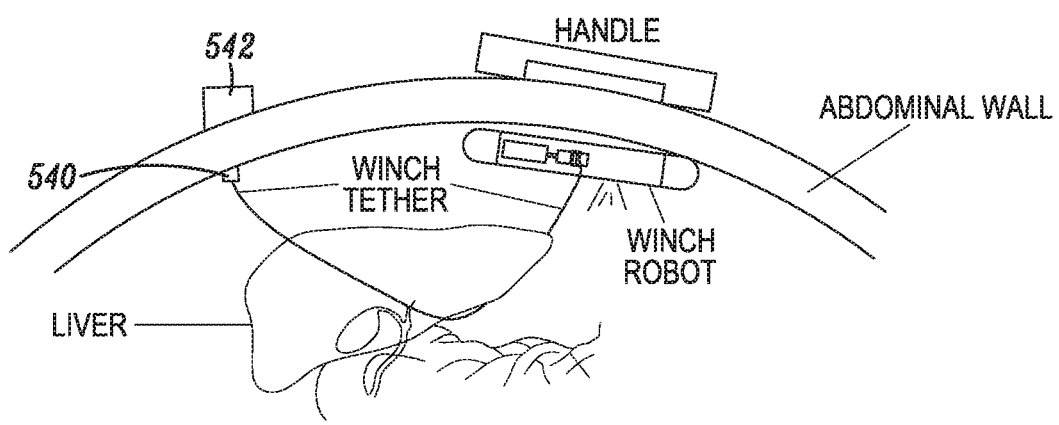
FIG. 21 shows a cutaway view of a medical device utilizing a winch component during a procedure in a patient, according to another embodiment.
Figure 22:
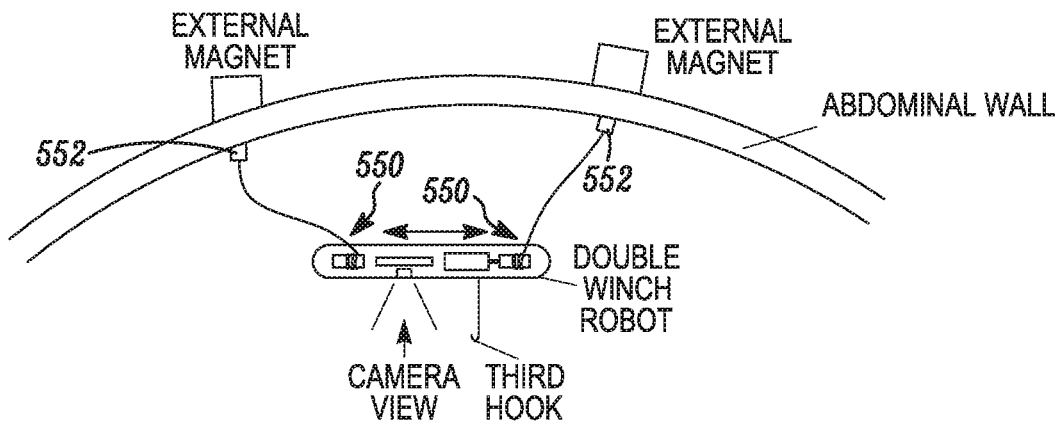
FIG. 22 is a cutaway view of a medical device utilizing two winch components during a procedure in a patient, according to yet another embodiment.

In another embodiment, the operational component can be a magnet 540 that can be held against the wall with a second handle 542 as depicted in FIG. 21. In a further embodiment, the device could have two winch components 550 with magnet operational components 552 that attach to two points in vivo as depicted in FIG. 22. Such a device could have two separate drums and motors, or alternatively, a single motor and drum.

The winch components and systems can be used to accomplish a variety of procedural tasks. In one embodiment, a device having a winch component could be used to retract an organ, such as the gallbladder, as depicted for example in FIG. 20. In another embodiment, a device having a winch component and a magnet operational component could be used as a sling to retract or move a very large organ such as the liver as depicted in FIG. 21. In yet another embodiment, the device is used as a "gantry crane" with two winch tethers attached to the abdominal wall, as depicted in FIG. 22, or to other organs. In this embodiment, the device is guided along the winch tethers to change the camera or illumination location. In another embodiment, the device could be guided along the winch tether, with a third winch hook (or grasper) below the device as shown in FIG. 22. This would allow the robot to reposition itself along the line of the first two tethers while the third winch could be used to grasp a tissue of interest for retraction or other manipulation. In yet another embodiment, the guide tethers are not suspended but lying on the organs.

In yet another alternative embodiment, the winch component can be any known configuration or be made up of any known components for use in a winch. Further, while certain device embodiments are described for exemplary purposes herein, it is understood that a winch component can be incorporated into any known robotic device for use inside a patient. For example, such a component can be incorporated into any of the devices disclosed in the applications that are incorporated herein elsewhere in this application.

Various additional embodiments disclosed herein relate to procedural devices with modular mechanical and electrical packages that can be used together in various combinations to provide capabilities such as obtaining multiple tissue samples, monitoring physiological parameters, and wireless command, control and data telemetry. This modular technology provides a flexible device into which one or more of various different components or systems can be integrated.

Current known minimally-invasive surgical technologies require two to three ports to accommodate the laparoscopic tools to explore the abdominal cavity and biopsy tissue of interest. The various embodiments of the devices and modular components disclosed herein require only one port for any medical procedure, thereby reducing patient trauma (1 incision rather than 2 or 3).

Figure 23A:
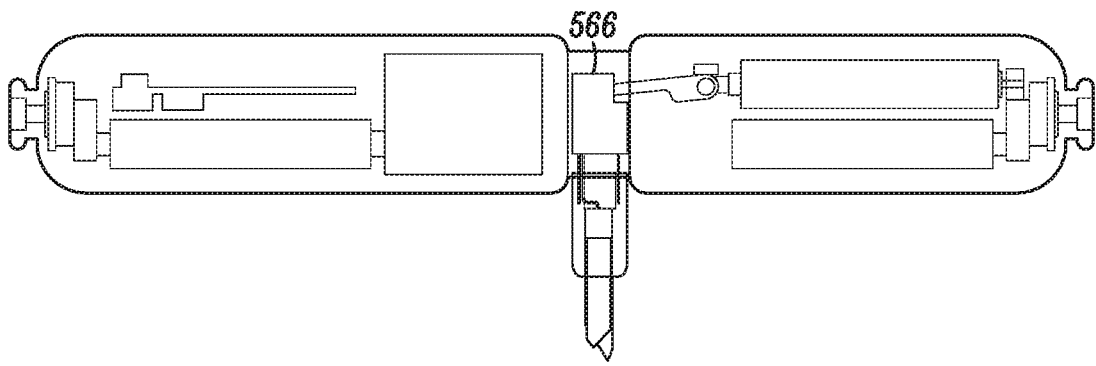
FIG. 23A depicts a front view of a medical device having a payload area that is a biopsy mechanism, according to one embodiment.

FIG. 23A depicts one exemplary implementation of a modular device having a payload area 566. The payload area 566 is configured to receive any one of several modular components, including such components as the sensor, controller, and biopsy components discussed herein. It is understood that in addition to the specific modular components disclosed herein, the payload areas of the various embodiments could receive any known component to be added to a medical procedural device.

Figure 23B:
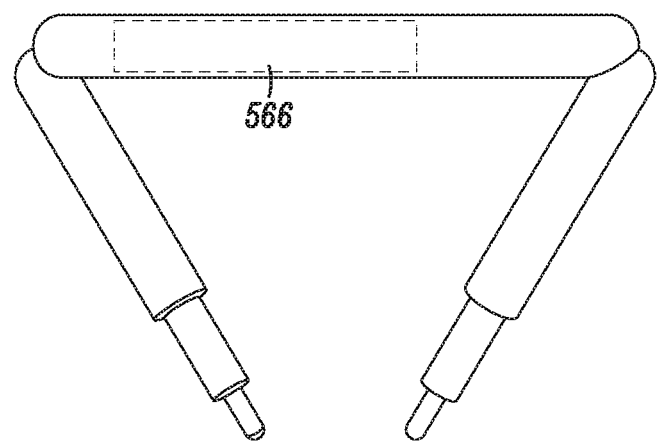
FIG. 23B shows a front view of a medical device having a payload area, according to another embodiment.

The modular technology disclosed herein can be incorporated into any type of medical procedural device and is not limited to the robotic devices described in detail herein. Certain device embodiments can be in vivo or robotic devices as defined herein, including devices configured to be positioned within a body cavity of a patient, including certain devices that can be positioned against or substantially adjacent to an interior cavity wall, and related systems. For example, FIG. 23B depicts a different device embodiment having a payload area 566. Thus, while the robotic device embodiments depicted in FIG. 23A is a mobile device having wheels, the various modular components described herein could just as readily be positioned or associated with a payload area in any other kind of robotic device or in vivo device such as the device depicted in FIG. 23B or can further be used in other medical devices and applications that don't relate to robotic devices.

Figure 24A:
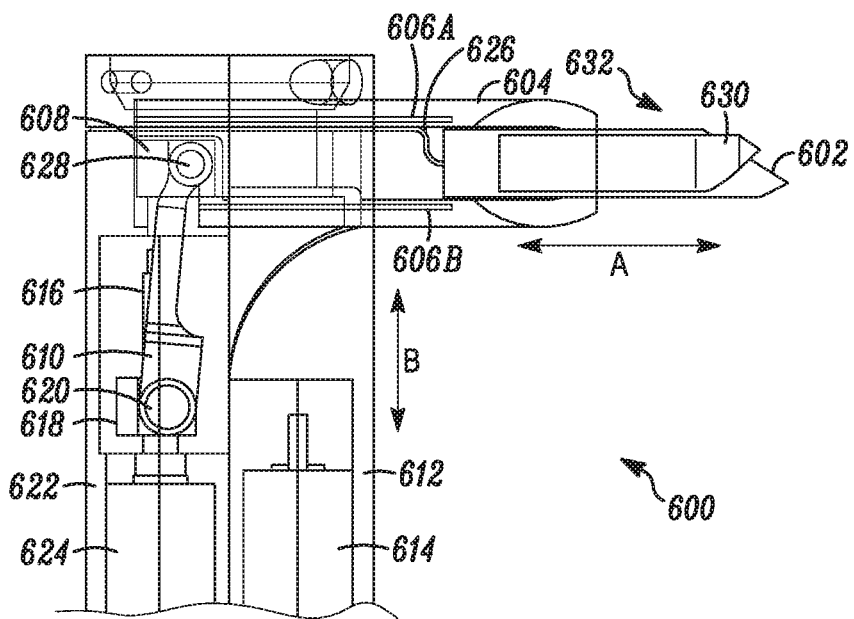
FIG. 24A is a side view of a modular biopsy mechanism, according to one embodiment. n.
Figure 24B:
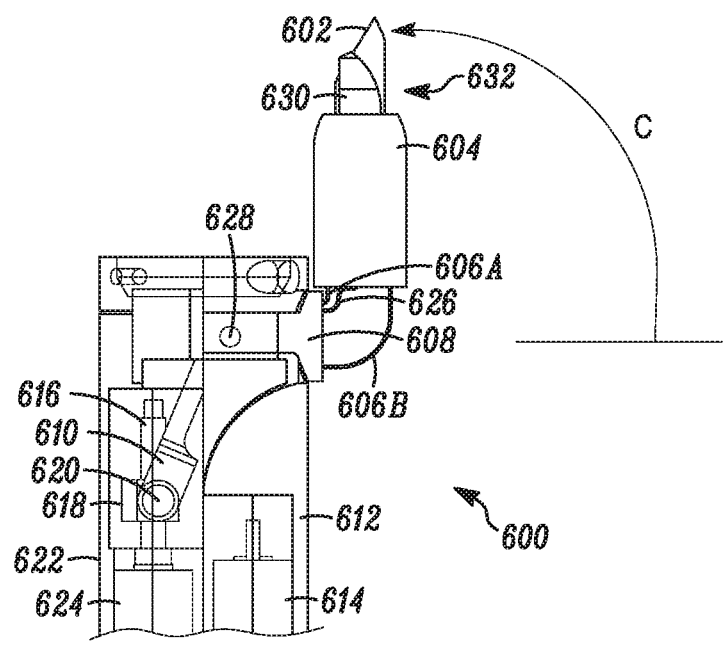
FIG. 24B depicts another side view of the modular biopsy component of FIG. 24A.
Figure 24C:
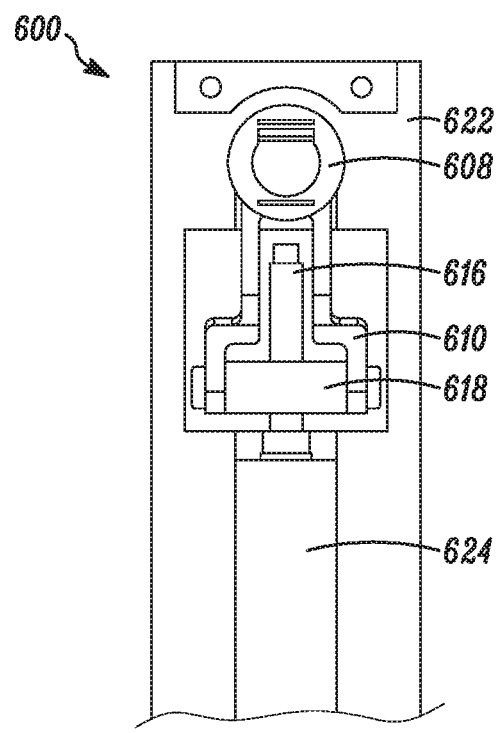
FIG. 24C shows a front view of the modular biopsy mechanism of FIGS. 24A and 24B.

FIGS. 24A, 24B, and 24C depict a biopsy component 600 according to one embodiment that can be used with any robotic device disclosed herein, including as shown for exemplary purposes in FIG. 23A or FIG. 23B. The mechanism 600 has a biopsy grasper 632 that in this implementation has a piercing or lower jaw component 602 and an upper jaw component 630. The piercing component 602 and jaw component 630 are structured like a pair of jaws, with the piercing component 602 being configured to remain stationary during the sampling process, providing a substantially rigid and stable base against which the upper jaw component 630 can move in a jaw-like fashion in relation to the piercing component 602 such that the jaw component 630 can ultimately make contact with the piercing component 602 and thereby cut the target tissue. Unlike standard laparoscopic biopsy tools that are generally designed to grasp tissue so that the surgeon can then tear the sample free, this grasper is designed to completely sever the sample from the tissue of interest without manual manipulation required by the surgeon or user.

In this embodiment, the upper jaw component 630 is moved in relation to the piercing component 602 via the collar 604. More specifically, the collar 604 is movably disposed over the piercing component 602 such that it can move back and forth in the direction indicated by arrow A. A proximal portion of the upper jaw component 630 is disposed between the piercing component 602 and the collar 604 and is configured to be positioned such that the distal end of the upper jaw 630 is not in contact with the piercing component 602 and remains in that position when no force is applied to the jaw 630. Thus, when the collar 604 is urged toward the distal end of the piercing component 602, the distal end of the upper jaw component 630 is urged toward the piercing component 602 such that the component 630 is capable of incising or cutting any tissue disposed between the upper jaw 630 and the piercing component 602 as the upper jaw 630 makes contact with the component 602. And when the collar 604 is urged away from the distal end of the piercing component 602, the distal end of the upper jaw 630 moves away from the piercing component 602 and toward its unrestrained position. Alternatively, it is understood that any known component that can operate in the same fashion as the collar to urge the upper jaw 630 into contact with the piercing component 602 can be incorporated herein.

The collar 604 is urged back and forth by the motor 624. It is understood that this embodiment is intended to encompass any actuation structure that urges the collar 634 to move back and forth such that the upper jaw component 630 is urged to move in relation to the piercing component 602 and thereby cut target tissue.

In this particular embodiment as shown in FIG. 24A, the grasper 632 is powered by the motor 624. Motor 624 is coupled to a nut 618 that is driven by the motor 624 along the axis of a lead screw 616 parallel to arrow B. The nut 618 is coupled to a slider 608 via a linkage 610 that is pivotally coupled to the nut at pin 620 and to the slider 618 at pin 628. The nut 618, linkage 610, and slider 608 convert the actuation direction from the direction of arrow B to the direction of arrow A and, according to one embodiment, increase the amount of force applied by the motor 624 to the slider 608.

The slider 608 is coupled to the collar 604 at two flexible components 606A, 606B, which can be shape-memory components 606A, 606B according to one embodiment. In one example, the flexible components 606A, 606B are comprised of nitinol. Further, the piercing component 602 is coupled to the housing 622 via a flexible component 626. According to one embodiment, the flexible component 626 is a shape-memory component 626 such as nitinol. These flexible components 606A, 606B, and 626 allow for the grasper 632 to be repositioned in relation to the rest of the robotic device to which it is coupled, as will be discussed in further detail below.

Alternatively, the actuation component and the connection of the actuation component to the collar 634 can be any known structure or component or combination thereof that provides motive force to actuate the grasper 632.

In one alternative implementation, the piercing component 602 has an internal reservoir (not shown) for storing one or more acquired samples. Unlike most standard laparoscopic biopsy tools that include space for only a single sample, this reservoir can be generally large enough or long enough (or otherwise has sufficient volume) to house multiple samples during a biopsy procedure.

In use, the biopsy component 600 is positioned next to the target tissue using a method such as the mobile robot wheel, or articulating robot arm. Next, the biopsy component 600 operates in the following manner to obtain a tissue sample. The motor 624 actuates the collar 604 to move toward the distal end of the piercing component 602 and thus actuates the upper jaw 630 to close and contact the piercing component 602. The tissue is cut as the upper jaw 630 is actuated towards the piercing component 602 in a slicing motion. In one embodiment the tissue sample is then stored in the piercing component 602 while additional samples are taken.

It is understood that the device containing the biopsy component 600 may also have other actuable components such as wheels, arms, etc. FIG. 24A further depicts a motor 614 disposed within a second housing 612 that is configured to actuate one or more additional actuable components of the device. In one example, the motor 614 can actuate a wheel (not shown) operably coupled with the device. In another example, this motor 614 actuates an arm (not shown) connected to the device.

In one aspect, the biopsy component 600 can also be configured to make it easier for the medical device to be inserted through incisions, transported, and stored. FIG. 24B depicts the grasper 632 of the biopsy component 600 positioned at a ninety degree angle in relation to its position in FIG. 24A. This re-positioning of the grasper 632 is accomplished due to the flexibility of the flexible components 606A, 606B, 626 as discussed above. According to one embodiment, this second position of the grasper 632 allows for easier insertion and retraction of the device to which the grasper is coupled. That is, the second position of the grasper 632 allows for the entire device to fit more easily through an incision, a port, or any other opening or device for use in medical procedures. In its operating position as depicted in FIG. 24A, the grasper 632 is positioned perpendicularly to the body of the robotic device to which it is coupled. The overall length of the robot body and grasper 632 is greater than the diameter of most laparoscopic trocars. Thus, to allow the robot/grasper 632 to be inserted through a trocar, the grasper 632 can be moved into a position that is parallel to the length of the robotic device using the support mechanism provided by the three flexible components 606A, 606B, 626 that provide both rigidity and the ability to flex the arm 640 degrees during insertion and retraction through a trocar or through any type of orifice, incision, or tool as necessary. This support mechanism provides the rigidity and forces required during biopsy sampling, with the flexibility required for insertion and retraction before and after the biopsy occurs.

Alternatively, a variety of alternative support mechanisms using this concept can be envisioned.

Figure 25A:
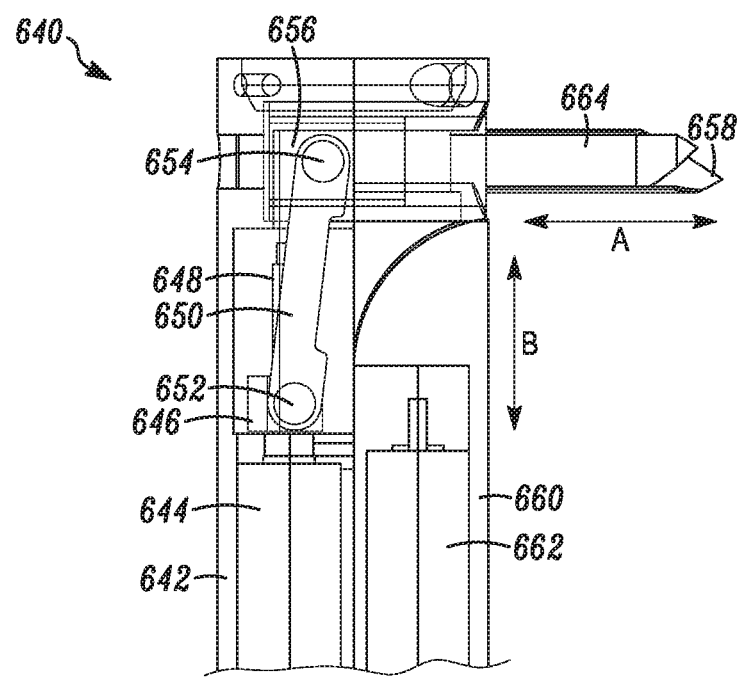
FIG. 25A is a side view of a modular biopsy mechanism, according to another embodiment.
Figure 25B:
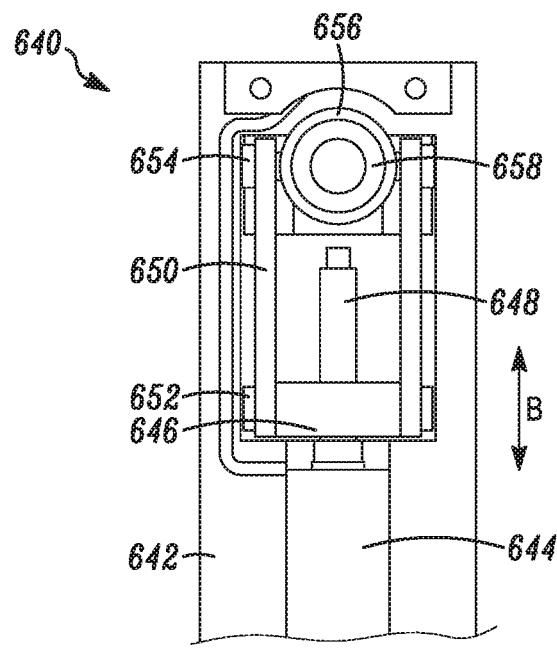
FIG. 25B depicts a front view of the modular biopsy mechanism of FIG. 25A.

FIG. 25A depicts an alternative embodiment of a biopsy component 640 that can be used with any robotic device disclosed herein. The component 640 has actuation components similar to those in the embodiment depicted in FIGS. 24A, 24B, and 24C, including a nut 646 driven along the axis of a lead screw 648 in the direction indicated by arrow B by a motor 644. The nut 646 is attached to a slider 656 via a linkage 650 that is coupled to the nut 646 at pin 652 and to the slider 656 at pin 650.

In this embodiment, the slider 656 performs generally the same function as the collar described in FIG. 24. That is, the slider 656 can move in the direction indicated by arrow A in relation to the piercing component 658. Thus, similarly to the collar as described above, as the slider 656 moves over the upper jaw 664, the upper jaw 664 is closed relative to the lower piercing jaw 658.

Figure 26:
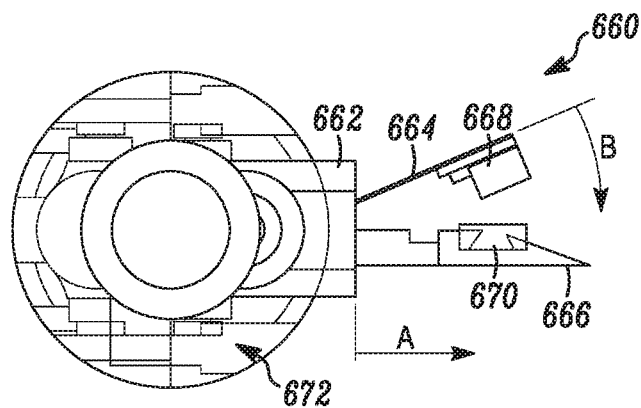
FIG. 26 shows a top view of a biopsy mechanism, according to another embodiment.

FIG. 26 depicts an alternative embodiment of the biopsy component 660 that can be used with any robotic device disclosed herein. The component 660 has actuation components similar to those in the embodiment depicted in FIGS. 24A, 24B, and 24C. In this embodiment the collar 662 is urged in the direction A. As the collar 662 moves forward it pushes the top jaw 664 downwards toward the bottom jaw 666 in direction B. The collar is held in place by the housing 672 in the same manner as described for FIG. 24.

Unlike other laparoscopic biopsy forceps in which both jaws are hinged about a pivot point, only one jaw, the top jaw 664, of the robotic grasper moves during sampling. The lower half of the grasper, bottom jaw 666, remains stationary and provides a rigid and stable base against which the top jaw 664 can cut. The fixed bottom jaw 666 is constructed from a hypodermic medical stainless steel tube and it forms a reservoir for storing multiple samples.

In one embodiment the profile of the top jaw 664 is constructed out of a super-elastic shape-memory nickel titanium alloy (Nitinol) ribbon (Memry Corporation) 0.25 mm thick and 3 mm wide. It is profiled such that the grasper is normally open. A wide variety of profiles can be achieved by heat-treating the ribbon for approximately 10 min at 500° C., followed by quenching in water. The Nitinol ribbon is glued to a fixed nylon rod insert that fits inside the bottom jaw 666.

The blades of the grasper are titanium nitrate coated stainless steel approximately 1.5 mm long. Small plastic inserts are fixed to the top and bottom jaws, and the blades 668 and 670 are glued to these inserts. The round blade 670 fixed to the bottom jaw has a diameter of 3 mm. The top blade 668 has a semi-circular profile with a diameter of 3.8 mm and overlaps the bottom blade when the jaw is closed. The sample is held within the bottom blade as the trailing edges of the top blade help sever the sample from the tissue.

Figure 27:
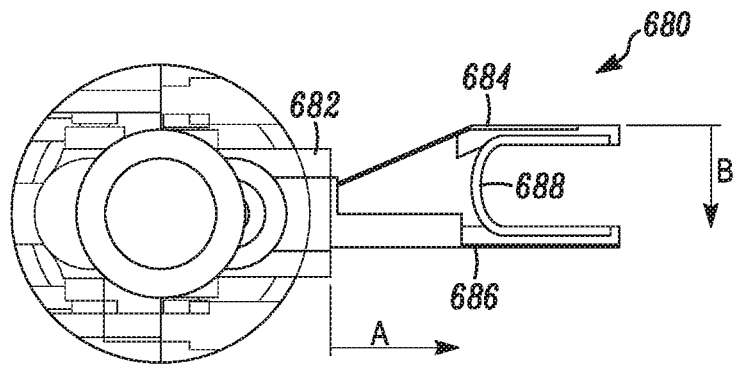
FIG. 27 is a top view of another biopsy mechanism, according to yet another embodiment.

FIG. 27 depicts an alternative embodiment of the biopsy component 680 that can be used with any robotic device disclosed herein to staple or clamp tissue. The component 680 has actuation components similar to those in the embodiment depicted in FIGS. 24A, 24B, and 24C. In this embodiment the collar 682 is urged in the direction A. As the collar 682 moves forward it pushes the top jaw 684 downwards toward the bottom jaw 686 in direction B. As the top jaw 684 is pressed downwards against the bottom jaw 686, a small surgical staple 688 can be compressed to staple tissue of interest or to clamp an artery or other vessel.

This stapling arm 680 was designed to hold and close a common laparoscopic surgical staple. In addition to stapling, this end effector can also be used for applications requiring clamping and holding, such as applying pressure to a bleeding blood vessel or manipulating other tissues of interest.

Figure 28A:
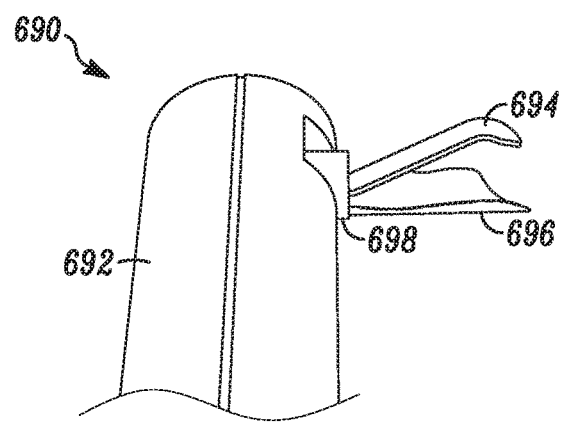
FIG. 28A depicts a perspective view of another biopsy mechanism, according to a further embodiment.
Figure 28B:
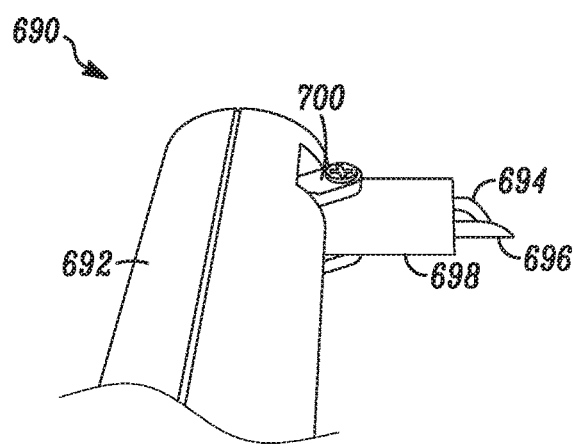
FIG. 28B shows a perspective view of the biopsy mechanism of FIG. 28A.

FIGS. 28A and 28B depict a further embodiment of a biopsy mechanism 690, according to one implementation. These two figures provide a detailed depiction of the opening and closing of grasper jaws 694, 696 according to one embodiment. More specifically, FIG. 28A depicts the mechanism 690 with the grasper jaws 694, 696 in their open configuration. In this configuration, the upper jaw 694 is in a position in which the distal end is not in contact with the distal end of the lower jaw 696.

FIG. 28B depicts the mechanism 690 with the grasper jaws 694, 696 in their closed configuration. That is, the collar 698 has moved from its retracted position in FIG. 28A to its extended position in FIG. 28B such that it has urged the upper jaw 694 down toward the lower jaw 696 such that the jaws 694, 696 ultimately reach the closed configuration.

Figure 29A:
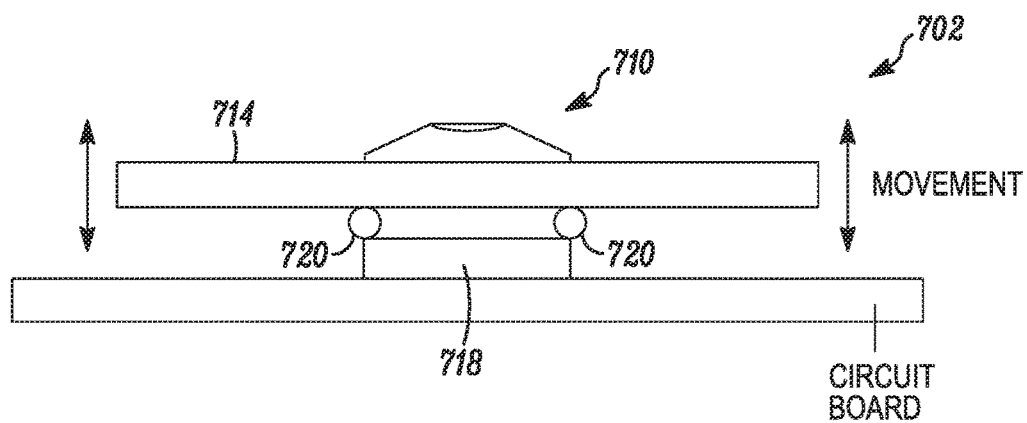
FIG. 29A is a side view of an adjustable focus component, according to one embodiment.
Figure 29B:
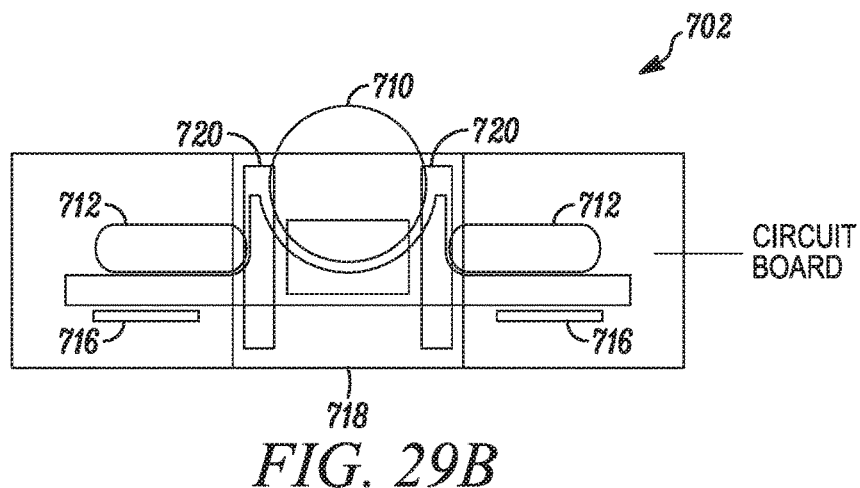
FIG. 29B depicts a top view of the adjustable focus component of FIG. 29A.
Figure 29C:
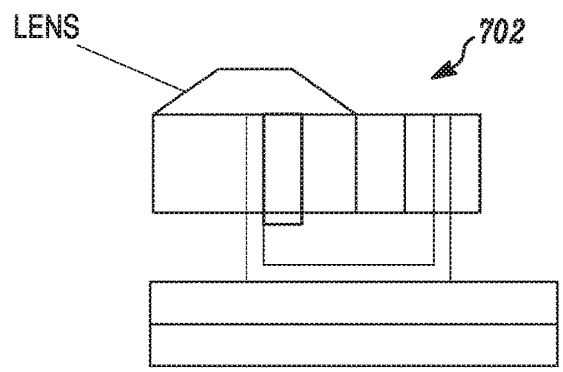
FIG. 29C shows an end view of the adjustable focus component of FIGS. 29A and 29B.
Figure 29D:
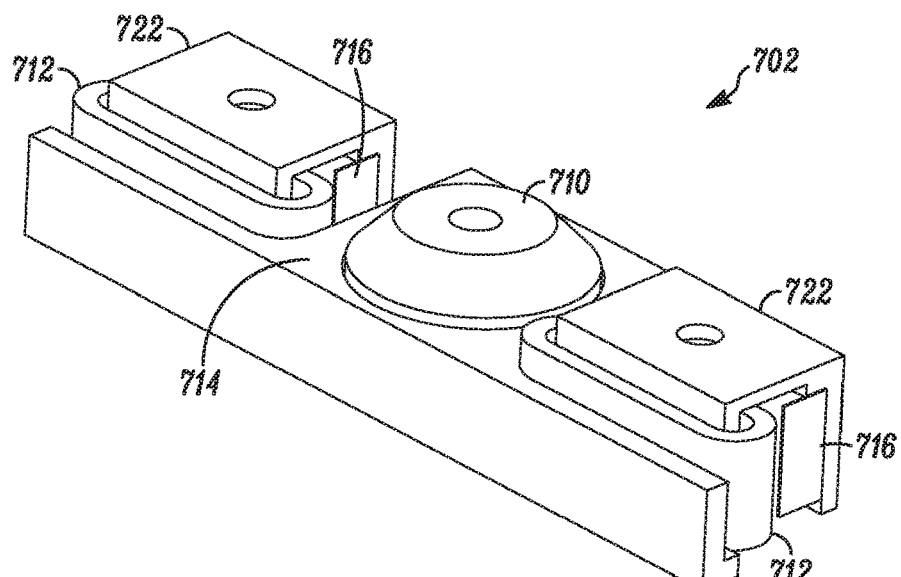
FIG. 29D is a perspective view of the adjustable focus component of FIGS. 29A, 29B, and 29C.
Figure 29E:
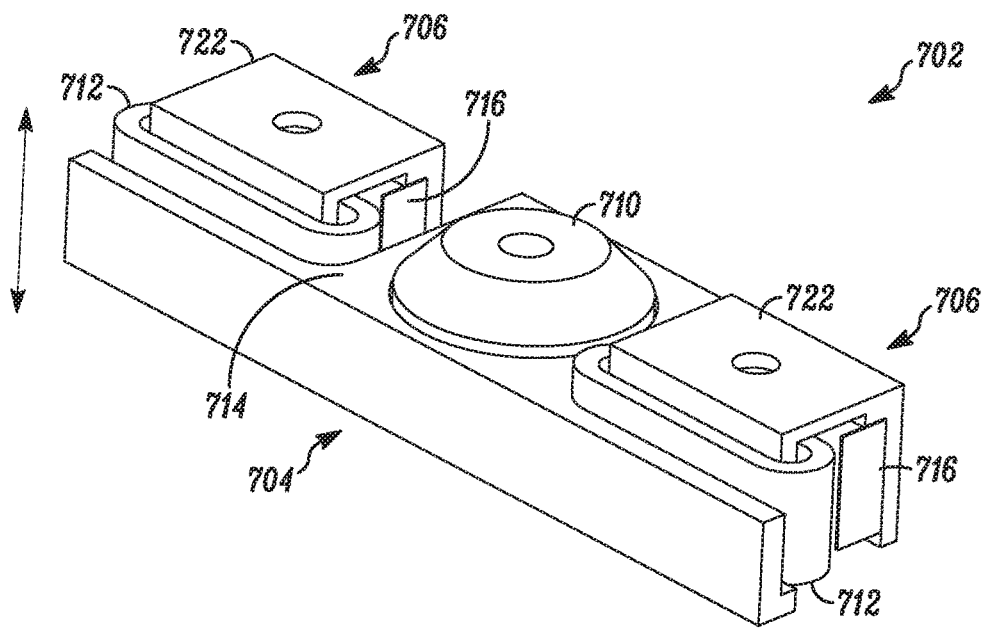
FIG. 29E depicts a perspective view of the adjustable focus component of FIGS. 29A, 29B, 29C, and 29D.

According to one embodiment, an imaging component in any medical device disclosed or incorporated herein having an imaging component can have an adjustable focus mechanism incorporated into or used with the imaging component. One exemplary implementation of such an adjustable focus mechanism 702 is depicted in FIGS. 29A, 29B, 29C, 29D, and 29E. As best shown in FIG. 29E, the mechanism 702 includes a lens subassembly 704 and two magnetic subassemblies 706. The lens subassembly 704 comprises a lens 710, two coils of wire 712 (as best shown in FIGS. 29B, 29D, and 29E), and a lens holding component 714 (as best shown in FIGS. 29A, 29D, and 29E) to hold the lenses 710 and coils 712 together in one subassembly. As best shown in FIGS. 29D and 29E, each magnetic subassembly 706 includes a small magnet 716 attached to one side of a U-channel 722 made from ferrous metal. The lens subassembly 704 is positioned between the two magnetic subassemblies 706. The coils 712 pass over the U-channels 722 and are positioned in the magnetic field that is generated between the small magnet 716 and the open side of the U-channel 722 where the coil 712 sits. As current is passed through the coiled wire 712 that is positioned in the magnetic field, an electromagnetic force is created that is parallel to the axis of the lens 710 and imager 718. This electromagnetic force is created by the magnetic field being perpendicular to the direction of the current.

In one embodiment, the small magnets 716 are Neodymium Magnets manufactured by K and J Magnetics of Jamison, Pa., the coils 712 are manufactured by Precision Econowind of North Fort Myers, Fla., and the lens 710 is manufactured by Sunex of Carlsbad, Calif. In this embodiment the magnets have a pull force of 2.17 lbs and a surface field of 2505 Gauss, while the coils are made of 120 turns of 36 AWG coated copper wire with a DSL758 lens. Alternatively, the above components can be any commercially available components.

According to one implementation, the lens holding component 714 is manufactured of polycarbonate plastic to minimize weight. In the embodiment shown in FIGS. 29D and 29E, the magnets 716 are 1/16"×1/8"×1/4" and the lens subassembly has a vertical stroke of 1 mm.

In one embodiment, a restoring force is provided that urges the lens 710 back to it resting position when the current from the coiled wire 712 is removed. This allows for consistent lens subassembly travel and can be used to maintain the lens in an optimum middle range of focus. According to one implementation, the restoring force component 720 as best shown in FIGS. 29A and 29B is a foam component 720. Alternatively, any known component for providing a restoring force can be used.

In accordance with one embodiment, the adjustable focus mechanism 702 is coupled with an auto focus algorithm to automatically command the mechanism 702 to focus the lens to a commanded depth. In a further embodiment, additional lens subassemblies 704 and magnetic subassemblies 706 can be combined to provide additional points of depth adjustment around the lens. These additional adjustment points allow a higher range of orientation angles of the lens to correct for any imperfections in manufacturing assembly. In this embodiment, the coils can be commanded separately to tilt the lens to correct for manufacturing error.

EXAMPLE

In this example, different biopsy grasper profiles and lengths were examined, including the effects of those profiles and lengths on the forces required to actuate the biopsy mechanism and further the maximum forces that could actually be applied by the mechanism.

Figure 30A:
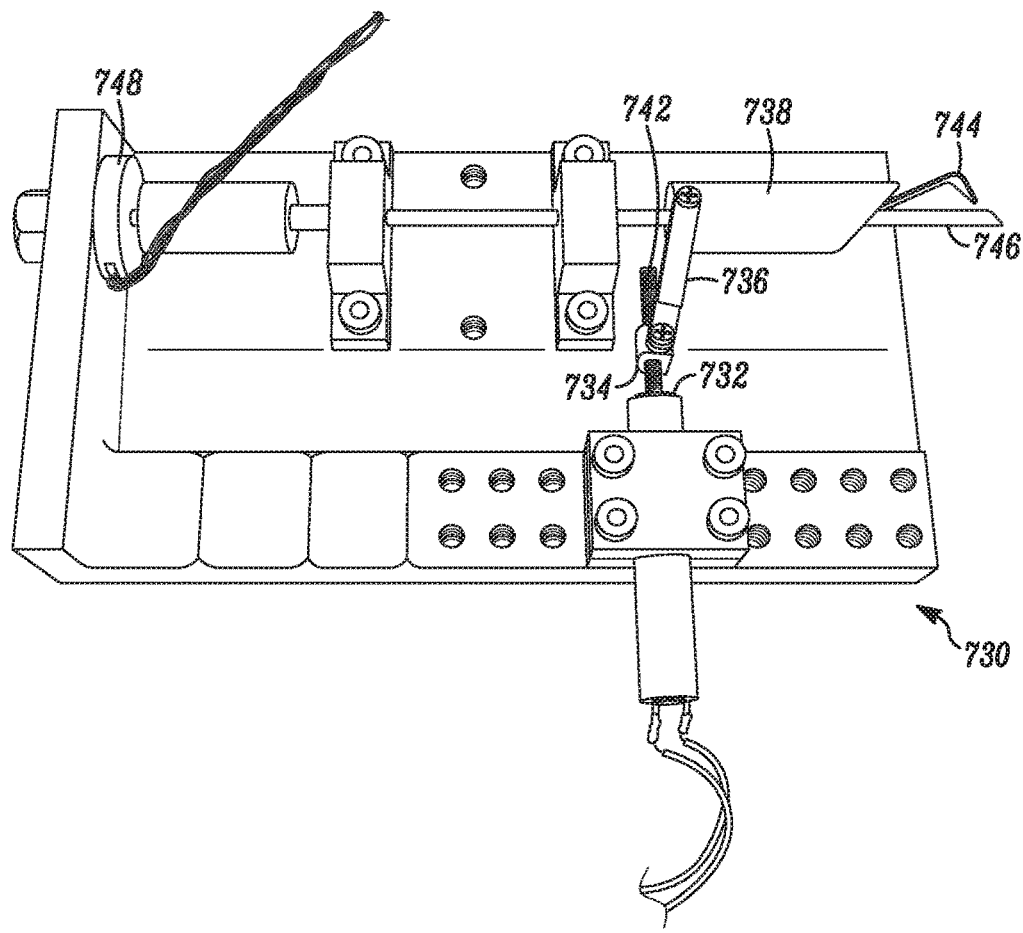
FIG. 30A shows a top view of a laboratory test jig used to measure forces applied by a biopsy mechanism, according to one embodiment.
Figure 30B:
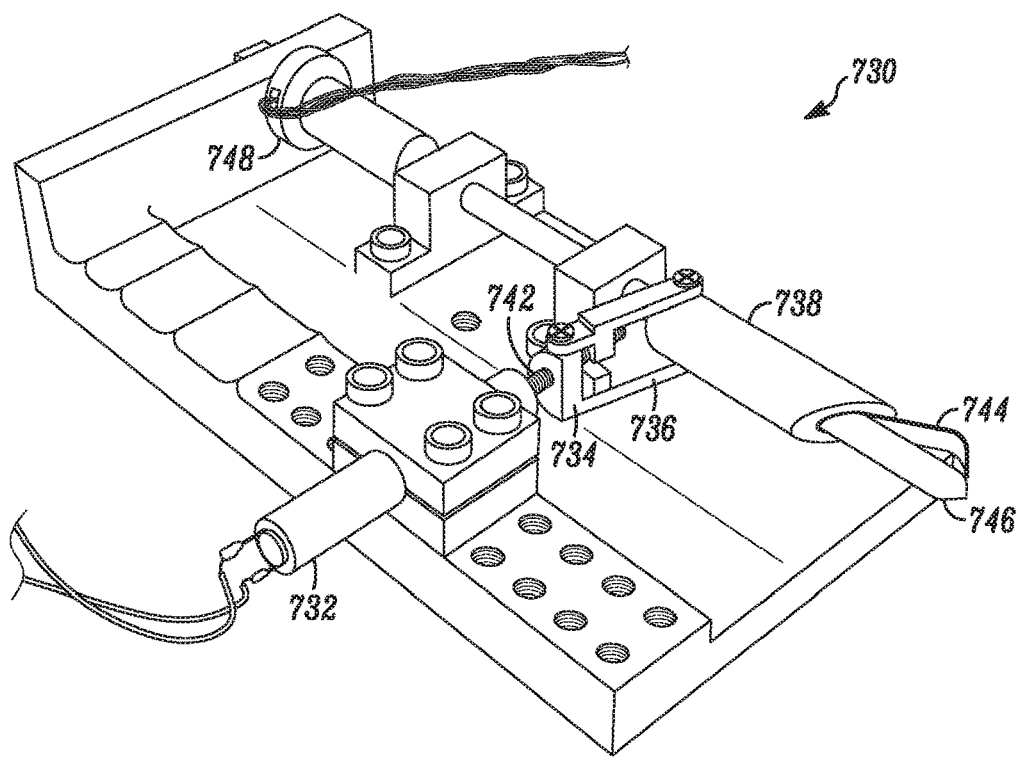
FIG. 30B is a perspective view of the test jig and biopsy mechanism of FIG. 30A.

FIGS. 30A and 30B depict a test jig 730 having a biopsy mechanism according to one embodiment. The test jig 730 as shown included a load cell 748 that was used to measure the tensile force in the nylon supporting rod when the collar 738 was actuated. Further, the biopsy mechanism of the jig 730 had a motor 732, linkage 736, lead nut 734, collar 738, lower jaw 746 and upper jaw 744.

Various grasper embodiments with a wide range of jaw lengths, opening angles, and jaw profiles were tested for actuation forces. Required actuation forces were determined by using the motor 732 and lead screw linkage 736 to slide the grasper collar 738 over the upper jaw 744 until closed. For each actuation, the required force was recorded starting with the upper jaw 744 completely open and continuing until the upper jaw 744 was closed. Maximum actuation forces were determined by recording the forces applied with the collar 738 held fixed at various positions corresponding to different times during actuation process. Each complete test consisted of 50 actuations of the biopsy grasper. Load cell data were recorded during each actuation at a rate of 20 Hz.

Figure 31:
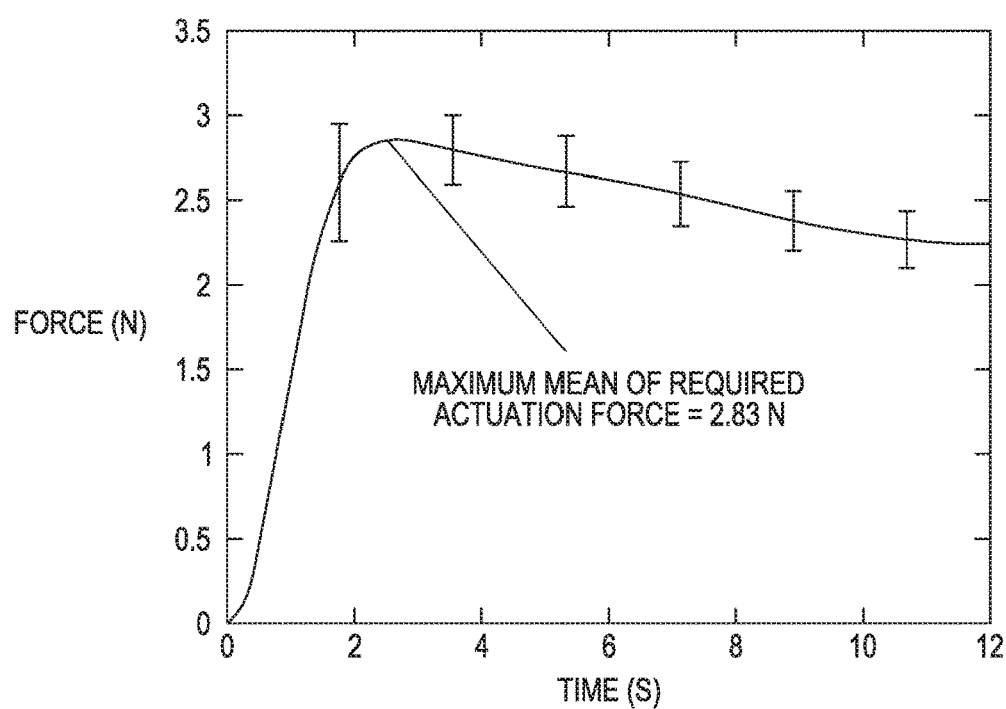
FIG. 31 depicts a line graph relating to data collected from the operation of the test jig depicted in FIGS. 30A and 30B.

FIG. 31 depicts the mean results from a required force test for a grasper that is approximately 12 mm long, has an opening angle of 25° and has a cutting tip with a length of 4 mm profiled with a closing angle of approximately 40°. The error bars indicate the standard deviation in the measured forces at intervals of approximately 1.8 seconds. The maximum required actuation force of 2.83 N is at the very start of the motion of the collar due to the need to overcome static friction and to begin flexing the top jaw of the grasper. The force decreases with time as the contact point between the collar and the top jaw moves farther away from the anchor point. The test results indicate that approximately a maximum of 3 N of force is required to close the biopsy grasper.

What is claimed is:
1. A robotic surgical system, comprising:
   (a) a tubular component comprising a distal end and a first lumen;
   (b) a robotic device sized to be positioned within a patient, the device comprising:
      (i) a first robotic arm comprising:
         (1) a first arm first link operably coupled to the tubular component via a first shoulder joint;
         (2) a first arm second link operably coupled to the first arm first link via a first elbow joint; and
         (3) a first operational component operably coupled to the first arm second link; and
      (ii) a second robotic arm comprising:
         (1) a second arm first link operably coupled to the tubular component via a second shoulder joint;
         (2) a second arm second link operably coupled to the second arm first link via a second elbow joint; and
         (3) a second operational component operably coupled to the second arm second link; and
   (c) at least one connection component disposed through the first lumen of the tubular component, the at least one connection component comprising a distal end operably coupled to the robotic device.
2. The robotic surgical system of claim 1, wherein the tubular component comprises at least one modular tube component.
3. The robotic surgical system of claim 1, wherein the tubular component comprises a plurality of modular tube components.
4. The robotic surgical system of claim 3, wherein the tubular component is a reversibly lockable tube.
5. The robotic surgical system of claim 1, further comprising a power source operably coupled to a proximal end of the at least one connection component.
6. The robotic surgical system of claim 1, wherein the at least one connection component comprises an electrical connection component.
7. The robotic surgical system of claim 1, wherein the at least one connection component comprises a hydraulic tube or a pneumatic tube.
8. The robotic surgical system of claim 1, further comprising an external controller operably coupled to a proximal end of the at least one connection component.
9. A robotic surgical system, comprising:
   (a) a tubular component comprising a first lumen, the tubular component configured to be positioned through an incision formed in a cavity wall of a patient;
   (b) a robotic device comprising:
      (i) a first robotic arm sized to be positioned in the cavity of the patient through the tubular component, the first robotic arm comprising:
         (1) a first arm first link operably coupled to the tubular component via a first shoulder joint at a first end of the first arm first link;
         (2) a first arm second link operably coupled to a second end of the first arm first link via a first elbow joint; and
         (3) a first operational component operably coupled to the first arm second link; and
      (ii) a second robotic arm sized to be positioned in the cavity of the patient through the tubular component, the second robotic arm comprising:
         (1) a second arm first link operably coupled to the tubular component via a second shoulder joint at a first end of the second arm first link;
         (2) a second arm second link operably coupled to a second end of the second arm first link via a second elbow joint; and
         (3) a second operational component operably coupled to the second arm second link; and
   (c) at least one connection component disposed through the first lumen of the tubular component, the at least one connection component comprising a distal end operably coupled to the robotic device.
10. The robotic surgical system of claim 9, further comprising a power source operably coupled to a proximal end of the at least one connection component.

11. The robotic surgical system of claim 9, wherein the at least one connection component comprises an electrical connection component.

12. The robotic surgical system of claim 9, wherein the at least one connection component comprises a hydraulic tube or a pneumatic tube.

13. The robotic surgical system of claim 9, wherein the tubular component comprises at least one modular tube component.

14. The robotic surgical system of claim 9, wherein the tubular component comprises a plurality of modular tube components.

15. The robotic surgical system of claim 14, wherein the tubular component is a reversibly lockable tube.

16. The robotic surgical system of claim 9, further comprising an external controller operably coupled to a proximal end of the at least one connection component.

17. A method of surgery comprising:
 providing a robotic system comprising:
  (a) a tubular component;
  (b) a robotic device comprising:
   (i) a first robotic arm comprising:
    (A) a first arm first link operably coupled to the tubular component via a first shoulder joint;
    (B) a first arm second link operably coupled to the first arm first link via a first elbow joint; and
    (C) a first operational component operably coupled to the first arm second link; and
   (ii) a second robotic arm comprising:
    (A) a second arm first link operably coupled to the tubular component via a second shoulder joint;
    (B) a second arm second link operably coupled to the second arm first link via a second elbow joint; and
    (C) a second operational component operably coupled to the second arm second link;
 inserting the robotic device into a body cavity through an incision in a wall of the body cavity such that the first and second robotic arms are positioned within the body cavity;
 coupling an external controller to the robotic device via a connection component disposed through the tubular component and operably coupled to the robotic device; and
 actuating the robotic device via the external controller and thereby performing a procedure with the first and second robotic arms within the body cavity.

18. The method of claim 17, further comprising adjusting the tubular component between a flexible configuration and a substantially rigid configuration.

19. The method of claim 17, further comprising placing the tubular component into a flexible configuration prior to inserting the robotic device into the body cavity.

20. The method of claim 17, further comprising placing the tubular component into a substantially rigid configuration when the robotic device is positioned within the body cavity.

* * * * *